(12) United States Patent
Smirnov et al.

(10) Patent No.: US 9,134,250 B2
(45) Date of Patent: Sep. 15, 2015

(54) SERS-SENSOR WITH NANOSTRUCTURED LAYER AND METHODS OF MAKING AND USING

(75) Inventors: Valery K. Smirnov, Yaroslavl (RU); Dmitry S. Kibalov, Yaroslavl (RU)

(73) Assignee: Wostec, Inc., San Francisco, CA (US)

( * ) Notice: Subject to any disclaimer, the term of this patent is extended or adjusted under 35 U.S.C. 154(b) by 0 days.

(21) Appl. No.: 14/385,750

(22) PCT Filed: Mar. 23, 2012

(86) PCT No.: PCT/RU2012/000210
§ 371 (c)(1),
(2), (4) Date: Sep. 16, 2014

(87) PCT Pub. No.: WO2013/141740
PCT Pub. Date: Sep. 26, 2013

(65) Prior Publication Data
US 2015/0077744 A1    Mar. 19, 2015

(51) Int. Cl.
| G01N 21/65 | (2006.01) |
| B81C 1/00 | (2006.01) |
| C23C 14/34 | (2006.01) |
| B82Y 15/00 | (2011.01) |
| B82Y 40/00 | (2011.01) |

(52) U.S. Cl.
CPC .......... *G01N 21/658* (2013.01); *B81C 1/00031* (2013.01); *C23C 14/3442* (2013.01); *B81C 2201/0143* (2013.01); *B82Y 15/00* (2013.01); *B82Y 40/00* (2013.01); *G01N 2201/06113* (2013.01); *Y10S 977/81* (2013.01)

(58) Field of Classification Search
CPC ............. G01N 21/658; B81C 1/00031; C23C 14/3442
USPC ......................................................... 356/301
See application file for complete search history.

(56) References Cited

U.S. PATENT DOCUMENTS

| 4,009,933 A | 3/1977 | Firester |
| 4,072,541 A | 2/1978 | Meulenberg et al. |
| 4,233,109 A | 11/1980 | Nishizawa |

(Continued)

FOREIGN PATENT DOCUMENTS

| RU | 2141699 C1 | 11/1999 |
| RU | 2152108 C1 | 6/2000 |

(Continued)

OTHER PUBLICATIONS

International Search Report and Written Opinion for PCT/RU2012/000210 mailed Dec. 20, 2012.

(Continued)

*Primary Examiner* — Kara E Geisel
*Assistant Examiner* — Hina F Ayub
(74) *Attorney, Agent, or Firm* — Lowe Graham Jones PLLC; Bruce E. Black

(57) ABSTRACT

A nanostructured arrangement includes a substrate having a surface and comprising a metal and a nanostructured layer formed on the substrate surface by an ion beam. The nanostructured layer includes a plurality of hollow metal nanospheres. Each of the plurality of nanospheres includes a chemical compound formed from the metal of the substrate by the ion beam. An example of a nanostructured arrangement is a surface enhanced Raman scattering (SERS) sensor.

25 Claims, 14 Drawing Sheets

(56) References Cited

U.S. PATENT DOCUMENTS

| | | |
|---|---|---|
| 4,400,409 A | 8/1983 | Izu et al. |
| 4,857,080 A | 8/1989 | Baker et al. |
| 5,160,618 A | 11/1992 | Burggraaf et al. |
| 5,498,278 A | 3/1996 | Edlund |
| 5,530,272 A | 6/1996 | Kudo et al. |
| 5,652,020 A | 7/1997 | Collins et al. |
| 5,702,503 A | 12/1997 | Tse Tang |
| 5,734,092 A | 3/1998 | Wang et al. |
| 5,753,014 A | 5/1998 | Van Rijn |
| 6,274,007 B1 | 8/2001 | Smirnov et al. |
| 6,417,939 B1 | 7/2002 | Laude |
| 6,452,724 B1 | 9/2002 | Hansen et al. |
| 6,518,194 B2 | 2/2003 | Winningham et al. |
| 6,580,172 B2 | 6/2003 | Mancini et al. |
| 6,667,240 B2 | 12/2003 | Ozaki et al. |
| 6,706,576 B1 | 3/2004 | Ngo et al. |
| 6,810,899 B2 | 11/2004 | Franz et al. |
| 6,954,275 B2 | 10/2005 | Choi et al. |
| 7,001,446 B2 | 2/2006 | Roark et al. |
| 7,175,694 B2 | 2/2007 | Ma et al. |
| 7,265,374 B2 | 9/2007 | Lee et al. |
| 7,338,275 B2 | 3/2008 | Choi et al. |
| 7,384,792 B1 | 6/2008 | Wang et al. |
| 7,453,565 B2 | 11/2008 | Wang et al. |
| 7,604,690 B2 | 10/2009 | Smirnov et al. |
| 7,768,018 B2 | 8/2010 | Smirnov et al. |
| 7,791,190 B2 | 9/2010 | Flores et al. |
| 7,977,252 B2 | 7/2011 | Smirnov et al. |
| 8,426,320 B2 | 4/2013 | Smirnov et al. |
| 8,859,440 B2 | 10/2014 | Smirnov et al. |
| 8,859,888 B2 | 10/2014 | Smirnov et al. |
| 2002/0142704 A1 | 10/2002 | Hu et al. |
| 2002/0154403 A1 | 10/2002 | Trotter |
| 2002/0170497 A1 * | 11/2002 | Smirnov et al. ........... 118/723 E |
| 2003/0152787 A1 | 8/2003 | Arakawa et al. |
| 2003/0171076 A1 | 9/2003 | Moloney et al. |
| 2003/0183270 A1 | 10/2003 | Falk et al. |
| 2003/0218744 A1 | 11/2003 | Shalaev et al. |
| 2004/0070829 A1 | 4/2004 | Kurtz et al. |
| 2004/0129135 A1 | 7/2004 | Roark et al. |
| 2004/0174596 A1 | 9/2004 | Umeki |
| 2004/0201890 A1 | 10/2004 | Crosby |
| 2004/0238851 A1 | 12/2004 | Flores et al. |
| 2005/0046943 A1 | 3/2005 | Suganuma |
| 2006/0205875 A1 | 9/2006 | Cha et al. |
| 2006/0230937 A1 | 10/2006 | Smirnov et al. |
| 2006/0273067 A1 | 12/2006 | Smirnov et al. |
| 2007/0012355 A1 | 1/2007 | LoCascio et al. |
| 2007/0082457 A1 | 4/2007 | Chou et al. |
| 2008/0072958 A1 | 3/2008 | Dutta |
| 2008/0119034 A1 | 5/2008 | Smirnov et al. |
| 2009/0118605 A1 | 5/2009 | Van Duyne et al. |
| 2009/0162966 A1 | 6/2009 | Jawarani et al. |
| 2010/0171949 A1 | 7/2010 | Mazur et al. |
| 2010/0300893 A1 | 12/2010 | Suh et al. |
| 2011/0232744 A1 | 9/2011 | Larsen et al. |
| 2011/0248386 A1 | 10/2011 | Smirnov et al. |
| 2014/0151715 A1 | 6/2014 | Smirnov et al. |
| 2014/0352779 A1 | 12/2014 | Smirnov et al. |
| 2015/0042988 A1 | 2/2015 | Smirnov et al. |

FOREIGN PATENT DOCUMENTS

| | | |
|---|---|---|
| RU | 2173003 C2 | 8/2001 |
| RU | 2180885 C1 | 3/2002 |
| RU | 2204179 C1 | 5/2003 |
| RU | 2231171 C1 | 6/2004 |
| RU | 2240280 C1 | 11/2004 |
| RU | 2321101 C1 | 3/2008 |
| TW | 200939471 A | 9/2009 |
| WO | 0017094 | 3/2000 |
| WO | 2005050697 A2 | 6/2005 |
| WO | 2010072862 | 7/2010 |
| WO | 2011044687 A1 | 4/2011 |
| WO | 2012009467 A1 | 1/2012 |

OTHER PUBLICATIONS

International Search Report and Written Opinion for International Patent Application No. PCT/RU2011/000489 mailed Mar. 1, 2012.
International Search Report and Written Opinion for International Patent Application No. PCT/RU2011/000631 mailed Mar. 1, 2012.
International Search Report and Written Opinion for International Patent Application No. PCT/RU2011/00594 mailed Apr. 19, 2012.
International Search Report and Written Opinion for International Patent Application No. PCT/US2006/011420 mailed Jun. 26, 2008.
International Search Report and Written Opinion for International Patent Application No. PCT/US2006/021564 mailed Jul. 28, 2008.
Karen, A. et al., "Quantitative Investigation of the O2+-Induved Topography of GaAs and other III-V Semiconductors: an STM Study of the Ripple Formation and Suppression of the Secondary Ion Yield Change by Sample Rotation," Surface and Interface Analysis, vol. 23, 1995, pp. 506-513.
Scott, K.L. et al., "Pattern Generators and Microcolumns for Ion Beam Lithography," Journal of Vacuum Science Technology B, 18(6) 2000, pp. 3172-3176.
Vajo, J.J. et al., "Influence of O2+ Energy, Flux, and Fluence on the Formation and Growth of Sputtering-Induced Ripple Topography on Silicon," Journal of Vacuum Science and Tecnology A. 14(5), 1996, pp. 2709-2720.
Official Communication for U.S. Appl. No. 11/421,384 mailed Aug. 21, 2008.
Official Communication for U.S. Appl. No. 11/421,384 mailed Apr. 24, 2009.
Official Communication for U.S. Appl. No. 11/421,384 mailed Sep. 3, 2009 Ii.
Official Communication for U.S. Appl. No. 13/164,387 mailed Sep. 6, 2012.
Official Communication for U.S. Appl. No. 13/407,615 mailed Mar. 28, 2014.
European Search Report for European Application No. 06851545.1 mailed Feb. 8, 2010.
Official Communication for U.S. Appl. No. 13/859,442 mailed Oct. 18, 2013.
Official Communication for U.S. Appl. No. 13/859,442 mailed May 2, 2014.
Official Communication for U.S. Appl. No. 13/859,442 mailed Mar. 27, 2014.
Official Communication for U.S. Appl. No. 11/100,175 mailed Oct. 24, 2007.
Official Communication for U.S. Appl. No. 11/100,175 mailed May 16, 2008.
Official Communication for U.S. Appl. No. 11/100,175 mailed Feb. 9, 2009
Chapter 7 in the book Sputtering by Particle Bombardment II: Sputtering of Alloys and Compounds, Electron and Neuron Sputtering, Surface Topography, Edited by R. Behrisch, 1983, Springer—Verlag, Berlin—Heidelberg—New York—Tokyo.
Mishra et al. Effect of initial target surface roughness on the evolution of ripple topography induced by oxygen sputtering of Al films, Journal of Applied Physics, vol. 105, 2009, 7 pages.
International Search Report and Written Opinion for PCT/RU2011/000977 mailed Sep. 6, 2012.
International Search Report and Written Opinion for PCT/RU2014/000458 mailed Feb. 5, 2015.
International Search Report and Written Opinion for PCT/RU2012/000016 mailed Sep. 13, 2012.

* cited by examiner

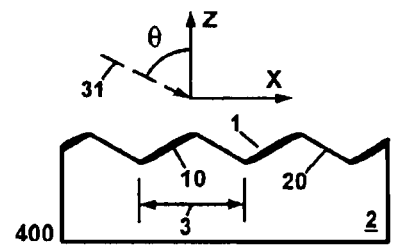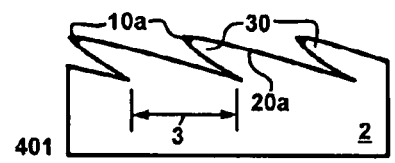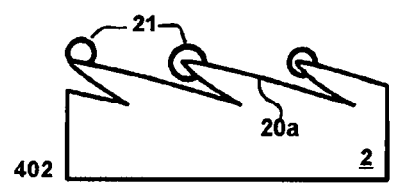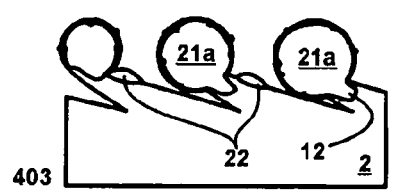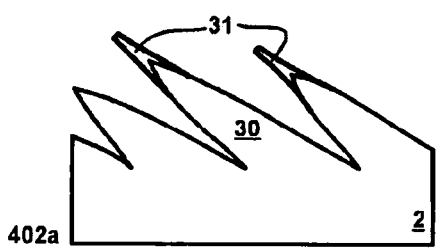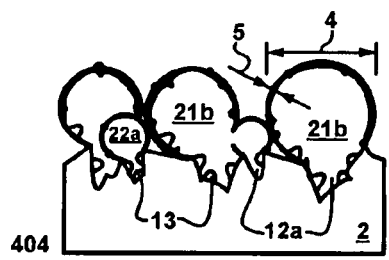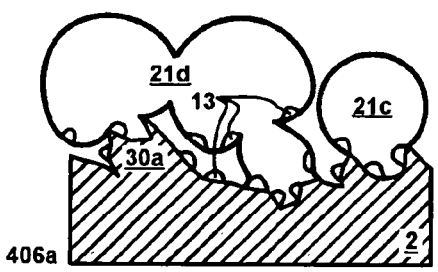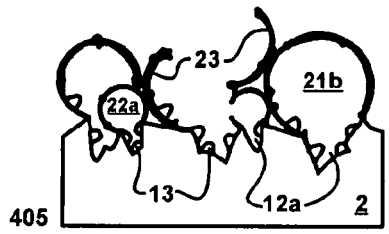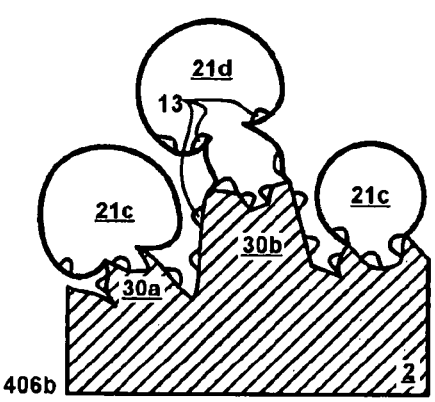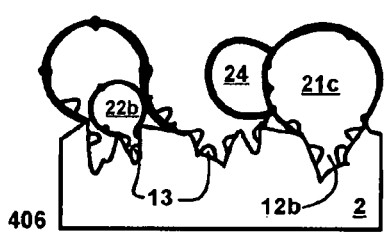
FIG. 2B
FIG. 2A

US 9,134,250 B2

SERS-SENSOR WITH NANOSTRUCTURED LAYER AND METHODS OF MAKING AND USING

CROSS-REFERENCE TO RELATED APPLICATIONS

This present application is a U.S. national stage application of PCT Application No. PCT/RU2012/000210, filed Mar. 23, 2012, which is hereby incorporated by reference in its entirety.

FIELD

The invention relates to the field of optical sensors for detecting and measuring the traces of organic compounds by the method of Raman spectroscopy using the effect of surface enhanced Raman scattering (SERS). The invention also relates to the technology of forming nanostructured elements on the surface of substrates for optical sensors (SERS-sensors) for measuring Raman scattering signal from analyte molecules positioned on the nanostructured surface of the sensor.

BACKGROUND

There is a general interest in the manufacture and use of optical sensors (SERS-sensors) with nanostructured metal surface. FIG. 13A illustrates one type of conventional SERS-sensor with nanostructured metal coverage. This SERS-sensor includes a substrate 132 of copper or silicon oxide, a dense hexagonal array of nanospheres 131 of polystyrene or silicon oxide arranged on the substrate surface, and a metal film 29a over the array of nanospheres (U.S. Patent Application Publication No. 2009/0118605, incorporated herein by reference). The diameter of the nanospheres is 390 nm and the thickness of metal film of silver is 200 nm. This reference also discloses examples of conventional SERS-sensors with a hexagonal array of metal triangles on the surface of the substrate. These sensors can be manufactured by nanosphere lithography (NSL) in which a monolayer of nanospheres is deposited on a substrate surface with dense hexagonal packing, metal is then deposited through the nanospheres, and then the nanospheres are removed. Disadvantages of the NSL method can include low throughput and difficulties in forming large area substrates. Disadvantages of conventional SERS-sensors can include a low surface density of the nanospheres and metal triangles in the arrays and small array sizes which may not surpass a few millimeters.

One type of conventional optical sensor is disclosed in U.S. Pat. No. 7,453,565, incorporated herein by reference. This SERS-sensor is illustrated in FIG. 13B and has a substrate 133 of aluminum, a template of nanopores in anodic aluminum oxide (AAO) 134, and silver nanoparticles 29 deposited in the nanopores of the AAO template. Between the nanoparticles 29 there are the gaps 14. Disadvantages of methods of manufacturing SERS-sensors based on AAO templates can include low throughput, difficulties in forming AAO templates of large area, and instability of the process of forming AAO templates induced by small deviations of critical parameters. A disadvantage of the conventional SERS-sensor can include a small size of the AAO template which may not surpass a few centimeters.

BRIEF SUMMARY

One embodiment is a surface enhanced Raman scattering (SERS) sensor including a substrate having a surface and comprising a metal; a nanostructured layer formed on the substrate surface by an ion beam; and a plurality of metal elements disposed, at least in part, on the plurality of nanospheres. The nanostructured layer includes a plurality of hollow metal nanospheres. Each nanosphere includes a chemical compound formed from the metal of the substrate by the ion beam.

Another embodiment is a method of making a SERS sensor. The method includes irradiating a surface of a substrate with a first ion beam to form a nanostructured layer on the substrate surface. The substrate includes a metal and the nanostructured layer includes a plurality of hollow metal nanospheres, each nanosphere having a chemical compound formed from the metal of the surface by the first ion beam.

Yet another embodiment is a nanostructured arrangement including a substrate having a surface and comprising a metal and a nanostructured layer formed on the substrate surface by an ion beam. The nanostructured layer includes a plurality of hollow metal nanospheres. Each of the plurality of nanospheres includes a chemical compound formed from the metal of the substrate by the ion beam.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 2A illustrates sequential schematic cross-sectional views of the formation of WOS-nanomask, conical elements and a layer of hollow nanospheres during an ion sputtering process, according to the invention;

FIG. 2B illustrates schematic cross-sectional views of conical hollow features and connected hollow nanospheres, according to the invention;

DETAILED DESCRIPTION

The invention relates to the field of optical sensors for detecting and measuring the traces of organic compounds by the method of Raman spectroscopy using the effect of surface enhanced Raman scattering (SERS). The invention also relates to the technology of forming nanostructured elements on the surface of substrates for optical sensors (SERS-sensors) for measuring Raman scattering signal from analyte molecules positioned on the nanostructured surface of the sensor.

For example, a SERS-sensor includes a substrate with a layer formed on the substrate surface by an ion beam. The layer includes thin-walled substantially closed hollow metal nanospheres, each nanosphere including a chemical compound formed from the metal by the ion beam. These nanospheres are self-formed during the irradiation of the metal substrate surface by a beam of chemically active gas ions forming a chemical compound with the metal. Ion bombardment may warm the substrate surface to near the melting temperature thus resulting in blistering and the formation of hollow nanospheres filled with the gas. The thickness of the nanosphere wall can be determined by the ion projection range, $R_p$, the average distance from the surface ions travel into the metal. In case of a low power ion beam having a low ion current density, which is insufficient for surface heating to near the melting temperature, additional separate heaters can be used, for example, lamps or resistive heaters to heat the substrate surface and to initiate blistering and the formation of hollow metal nanospheres.

Figure 10A:
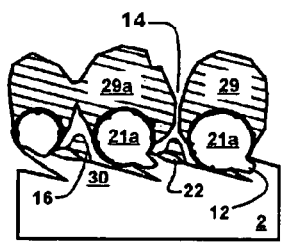
FIGS. 10A to 10D are schematic cross-sectional views of embodiments of a SERS-sensor including a layer of hollow substantially closed metal nanospheres on the surface of a metal substrate covered by a SERS active metal, according to the invention.

FIG. 10A illustrates one embodiment of a SERS-sensor that includes a substrate 2, for example, of aluminum with a layer of nanospheres 21a on the tops of conical elements 30. The nanosphere shape can be regular or irregular and nanosphere surface can be smooth or rough. Small blisters 22 can occur on the surface of conical elements 30. The conical elements 30 can be positioned obliquely with respect to the substrate plane. Separated metal elements 29 and connected metal elements 29a are located on the surface of the nanospheres 21a. There may also be gaps 14. Metal islands 16 can occur in the spaces between the nanospheres. Metal islands 16 are not connected to other metal elements and are considerably smaller in size compared to other metal elements. Connected metal elements 29a can be positioned over at least two nanospheres.

Figure 10B:
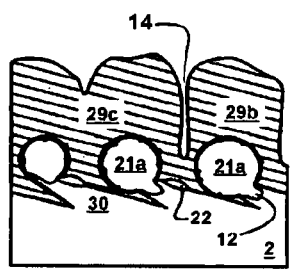

FIG. 10B illustrates an embodiment of a SERS-sensor, in which the metal can fill the spaces or nanotrenches between nanospheres 21a down to their bottom. Separated metal elements 29b and connected metal elements 29c are located on the surface of the nanospheres 21a and there may be gaps 14. Connected metal elements 29c can be positioned over at least two nanospheres.

Figure 10C:
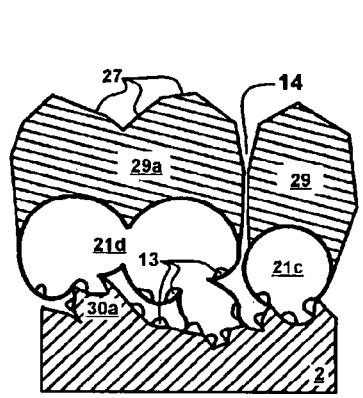

FIG. 10C illustrates an embodiment of a SERS-sensor, in which the nanospheres are connected to form a multichamber structure 21d. Some nanospheres of these multichamber structures and separated nanospheres 21c can be connected to the bases of ridge elements 30a. Fine porous structure including small pores 13, which are mostly closed pores of 5-15 nm in size having walls of about 5 nm, can occur on the surface of the substrate and inside the nanospheres. Separated metal elements 29 and connected metal elements 29a are located on the surface of the nanospheres 21a and multichamber structures 21d and there may be gaps 14. Connected metal elements 29a can be positioned over at least two nanospheres or two chambers of a multichamber structure. Flat grain facets 27, which are mostly polygons of 10-100 nm in size, can occur on the surface of the metal elements 29 and 29a.

Figure 10D:
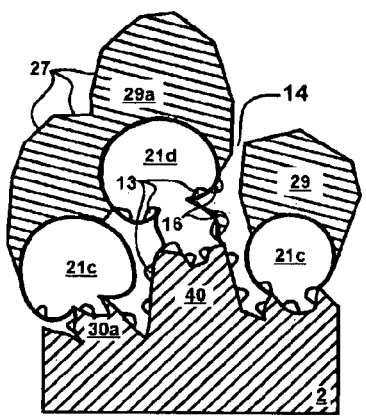

FIG. 10D illustrates an embodiment of a SERS-sensor, in which the substrate can be nonplanar and can have protrusions 40 on the surface. In this embodiment the islands 16 of SERS active metal can occur on the surface of nanospheres and multichamber structures 21d composed from connected hollow nanospheres. Fine porous structure including small pores 13 can occur on the surface of the substrate, within nanospheres, and within multichamber structures. Separated metal elements 29 and connected metal elements 29a are located on the surface of the nanospheres 21a and multichamber structures 21d with the gaps 14. Connected metal elements 29a can be positioned over at least two nanospheres or two chambers of multichamber structures. Flat grain facets 27 can occur on the surface of the metal elements 29 and 29a.

Figure 11A:
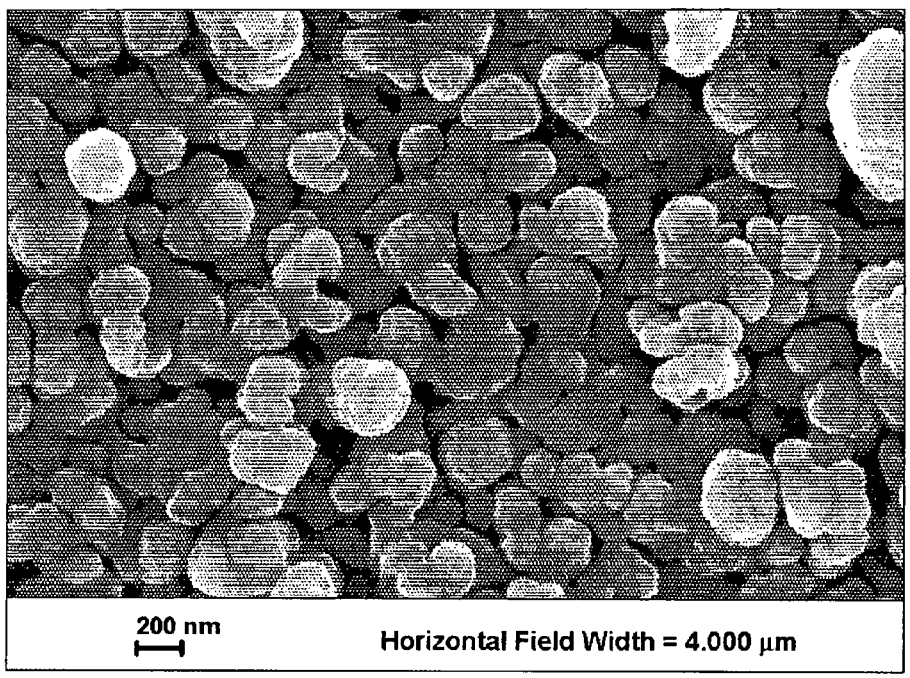
FIG. 11A is a SEM top view of an embodiment of a SERS-sensor including a layer of hollow substantially closed aluminum nanospheres on the surface of an aluminum substrate covered by silver with a mass-equivalent thickness of about 200 nm, according to the invention.

FIG. 11A is a SEM top view of the SERS-sensor including a layer of hollow aluminum nanospheres on the surface of an aluminum substrate having a silver coverage with a mass-equivalent thickness of about 200 nm. This layer of hollow aluminum nanospheres is formed by irradiating the surface of the aluminum substrate using a $N_2^+$ ion beam with energy E=5 keV at an angle of bombardment θ=53° from surface normal with ion fluence of $5 \times 10^{17}$ cm$^{-2}$ and ion current density of 1 mA/cm$^2$. The nanosphere shells are composed of aluminum with the addition of ion synthesized aluminum nitride and nitrogen atoms. In this example, the diameter of the nanospheres ranges from 50 to 350 nm and the average diameter of the nanospheres is about 150 nm.

Figure 11B:
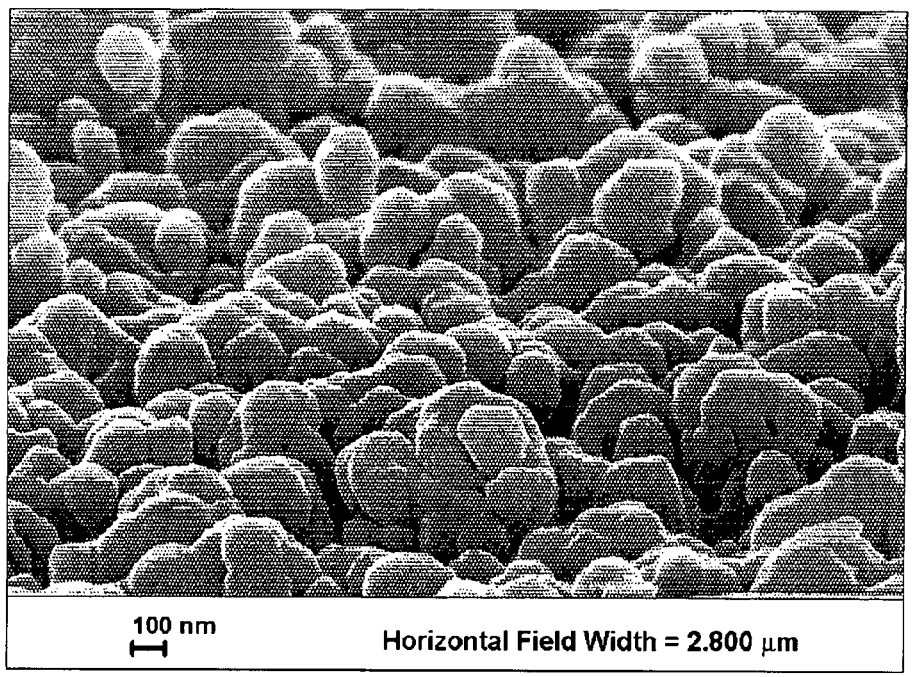
FIG. 11B is a SEM view, angled at 70°, of the SERS-sensor of FIG. 11A, according to the invention.

FIG. 11B is a SEM view, angled at 70°, of the SERS-sensor shown in FIG. 11A. One can see the flat grain facets of silver coverage and gaps between silver metal elements.

One distinctive feature of these embodiments of the SERS-sensor over conventional SERS-sensors is that the size of the nanostructured surface of the substrate can be considerably enlarged compared to the size of the AAO template and the array of nanospheres of conventional SERS-sensors. In at least some embodiments of the present SERS-sensors, the possible size of the nanostructured surface of the substrate is determined by the size of the ion beam. In at least some embodiments, this can be as large as 300 mm or more.

The embodiments of FIGS. 10A to 10D and 11A to 11B are examples of SERS-sensors. It will be understood that other types of SERS-sensor configurations can be modified to include a nanostructured layer. It will also be understood that the embodiments described above can include a modified nanostructured layer using known etching methods including ion sputtering, dry and wet etching. For example, substantially closed nanospheres can be transformed into substantially opened nanospheres by ion sputtering or reactive ion etching (RIE) in plasma or by wet etching. It will also be understood that metal plates or foils or metal films deposited on other suitable carrier materials can be used as substrates to form the nanostructured layer of hollow metal nanospheres by the ion beams. For example, chemically active gas ion beams, nitrogen or oxygen, can be used to make the nanostructured layer of hollow nanospheres of aluminum or titanium on the surface of substrates of aluminum or titanium, respectively. In these cases depending on gas ions used the nanospheres may include aluminum nitride or aluminum oxide or titanium nitride or titanium oxide.

In at least some embodiments, the size of the nanospheres is determined by a period of a wavelike aluminum nitride hard nanomask formed on the aluminum surface by a nitrogen ion beam. Examples of methods of forming a similar silicon nitride nanomask on a silicon wafer are described in U.S. Pat. No. 7,768,018 and U.S. Patent Application Publication No. 2008/0119034, both of which are incorporated herein by reference. Examples of ultra thin membranes based on wave-ordered structure patterns are described in U.S. Pat. No. 7,604,690, which is incorporated herein by reference. In at least some embodiments, a wavelike aluminum nitride nanomask is formed by irradiation of the surface of an aluminum substrate by a beam of nitrogen ions. Further sputtering by a beam of nitrogen ions may create a conical structure, which then may transform into a layer of nanospheres. In at least some embodiments, the average diameter of the nanospheres is controllably varied in a range from 20 to 150 nm (or 20 to 200 nm or 20 to 400 nm) to increase the performance of SERS-sensors.

In at least some embodiments, a hard nanomask includes a quasi-periodic, anisotropic array of elongated elements having a wave-ordered structure pattern and a wavelike cross-section. At least some of the elements have the following structure in cross-section: an inner region of metal and a first outer region of chemical compound covering a first portion of the inner region and being formed from metal by the ion beam. In at least some embodiments, the first outer regions form a net-like or an island-like structure or any combination thereof. In at least some embodiments, the average period of the array is in a range from 20 to 150 nm (or 20 to 200 nm or 20 to 400 nm).

In at least some embodiments, the nanomask further includes, in cross-section, a second outer region of chemical compound formed from the metal by irradiation using the ion beam. This second outer region covers a second portion of the inner region and connects with the first outer region at a wave crest where the first outer region is substantially thicker than the second outer region. In at least some embodiments, in cross-section the thickness of the second outer region is relatively small or minimal in the middle and increases from the middle towards its borders.

In at least some embodiments, aluminum or titanium can be used as metals in the wavelike hard nanomask. In at least some embodiments, the outer regions of the hard nanomask may include aluminum nitride, aluminum oxide, titanium nitride, or titanium oxide. In at least some embodiments, instead of pure metals their alloys can be used.

In at least some embodiments, for a beam of nitrogen ions with $N^+$ ions and $N_2^+$ ions in the relative fractions of x and (1−x), respectively, the nanomask average period, the nanomask formation depth, and the ion dose to form the nanomask are (1+x) times greater than those for a $N_2^+$ ion beam. In at least some embodiments, the ion dose for an $N_2^+$ ion beam is in the range $1 \times 10^{17}$–$5 \times 10^{18}$ cm$^{-2}$ and the maximum thickness of the first outer region is determined by the formula: T=2(1+x)E, where T is the thickness in nm and E is the ion beam energy in keV.

In at least some embodiments, the nanomask is formed by irradiating the aluminum surface using an oblique beam of nitrogen ions until a hard nanomask is formed, the nanomask elements being substantially perpendicular to the projection of the ion flow on the aluminum surface.

In at least some embodiments, a nanostructured layer having a plurality of hollow aluminum nanospheres is formed from a hard nanomask of aluminum nitride. The nanomask includes a quasi-periodic, anisotropic array of elongated elements having a wave-ordered structure pattern and a wavelike cross-section. At least some of the elongated elements have the following structure in cross-section: an inner region of aluminum and a first outer region of aluminum nitride covering a first portion of the inner region and being formed from aluminum by a nitrogen ion beam. In at least some embodiments, an aluminum foil or aluminum layer deposited on the surface of the other carrier material is used as an aluminum substrate.

The wave like topography or ripples, which self-forms on aluminum surface by the oxygen ion beam, is known (Mishra P., Ghose D. Effect of initial target surface roughness on the evolution of ripple topography induced by oxygen sputtering of Al films, Journal of Applied Physics, Volume 105, 2009, pp. 014304, incorporated herein by reference). However, the wavelike nanomask on aluminum, which is formed by oxygen ion beam and includes the thick and thin outer regions of aluminum oxide connecting at the wave crest, is not known in the prior art as well as wave like nanomasks on titanium formed by nitrogen or oxygen ion beams.

In at least some embodiments, a nanostructured layer having a plurality of hollow aluminum nanospheres is formed from a hard nanomask of aluminum oxide. The nanomask includes a quasi-periodic, anisotropic array of elongated elements having a wave-ordered structure pattern and a wavelike cross-section. At least some of the elongated elements have the following structure in cross-section: an inner region of aluminum and a first outer region of aluminum oxide covering a first portion of the inner region and being formed from aluminum by an oxygen ion beam.

In at least some embodiments, a nanostructured layer having a plurality of hollow titanium nanospheres is formed from a hard nanomask of titanium oxide. The nanomask includes a quasi-periodic, anisotropic array of elongated elements having a wave-ordered structure pattern and a wavelike cross-section. At least some of the elongated elements have the following structure in cross-section: an inner region of titanium and a first outer region of titanium oxide covering a first portion of the inner region and being formed from titanium by an oxygen ion beam.

In at least some embodiments, a nanostructured layer having a plurality of hollow titanium nanospheres is formed from a hard nanomask of titanium nitride. The nanomask includes a quasi-periodic, anisotropic array of elongated elements having a wave-ordered structure pattern and a wavelike cross-section. At least some of the elongated elements have the following structure in cross-section: an inner region of titanium and a first outer region of titanium nitride covering a first portion of the inner region and being formed from titanium by a nitrogen ion beam.

One embodiment of a method for nanostructuring the surface of an aluminum substrate for a SERS-sensor includes irradiating a surface of the substrate with a beam of nitrogen ions until a nanostructured layer is formed. The layer includes hollow aluminum nanospheres, each nanosphere including aluminum nitride formed from the aluminum by the nitrogen ion beam. In at least some embodiments, the method further includes heating the substrate to near melting temperature of aluminum to induce the formation of hollow aluminum nanospheres.

One embodiment of a method for nanostructuring the surface of an aluminum substrate for a SERS-sensor includes irradiating a surface of the substrate with a beam of oxygen ions until a nanostructured layer is formed. The layer includes hollow aluminum nanospheres, each nanosphere including aluminum oxide formed from the aluminum by the oxygen ion beam.

One embodiment of a method for nanostructuring the surface of an aluminum substrate for a SERS-sensor includes irradiating a surface of the substrate with a beam of nitrogen ions until a first nanostructured layer is formed. The first layer includes conical features of aluminum directed towards the nitrogen ion beam. The method further includes irradiating a surface of the first nanostructured layer with a beam of oxygen ions until a second nanostructured layer is formed. The second layer includes hollow aluminum nanospheres, each nanosphere including aluminum oxide formed from the aluminum by the oxygen ion beam.

One embodiment of a method for nanostructuring the surface of a titanium substrate for a SERS-sensor includes irradiating a surface of the substrate with a beam of oxygen ions until a nanostructured layer is formed. The layer includes hollow titanium nanospheres, each nanosphere including titanium oxide formed from the titanium by the oxygen ion beam.

One embodiment of a method for nanostructuring the surface of a titanium substrate for a SERS-sensor includes irradiating a surface of the substrate with a beam of nitrogen ions until a nanostructured layer is formed. The layer includes hollow titanium nanospheres, each nanosphere including titanium nitride formed from the titanium by the nitrogen ion beam.

One embodiment of a method for nanostructuring the surface of a titanium substrate for a SERS-sensor includes irradiating a surface of the substrate with a beam of nitrogen ions until a first nanostructured layer is formed. The first layer includes conical features of titanium directed towards the nitrogen ion beam. The method further includes irradiating a surface of the first nanostructured layer with a beam of oxygen ions until a second nanostructured layer is formed. The second layer includes hollow titanium nanospheres, each nanosphere including titanium oxide formed from the titanium by the oxygen ion beam.

In at least some embodiments, a SERS-sensor includes a substrate with a nanostructured layer and coverage of SERS-active metal over the nanostructured layer. In at least some embodiments, the metal coverage includes at least one metal from the group of silver, gold, copper, platinum, palladium, rhodium, ruthenium, osmium, iridium, iron, cobalt, nickel, and aluminum. In at least some embodiments, the SERS-active metal is deposited by methods including, but not limited to, plasma enhanced magnetron sputtering of a metal target, thermal evaporation of metal, or metal deposition from a solution.

Figure 1A:
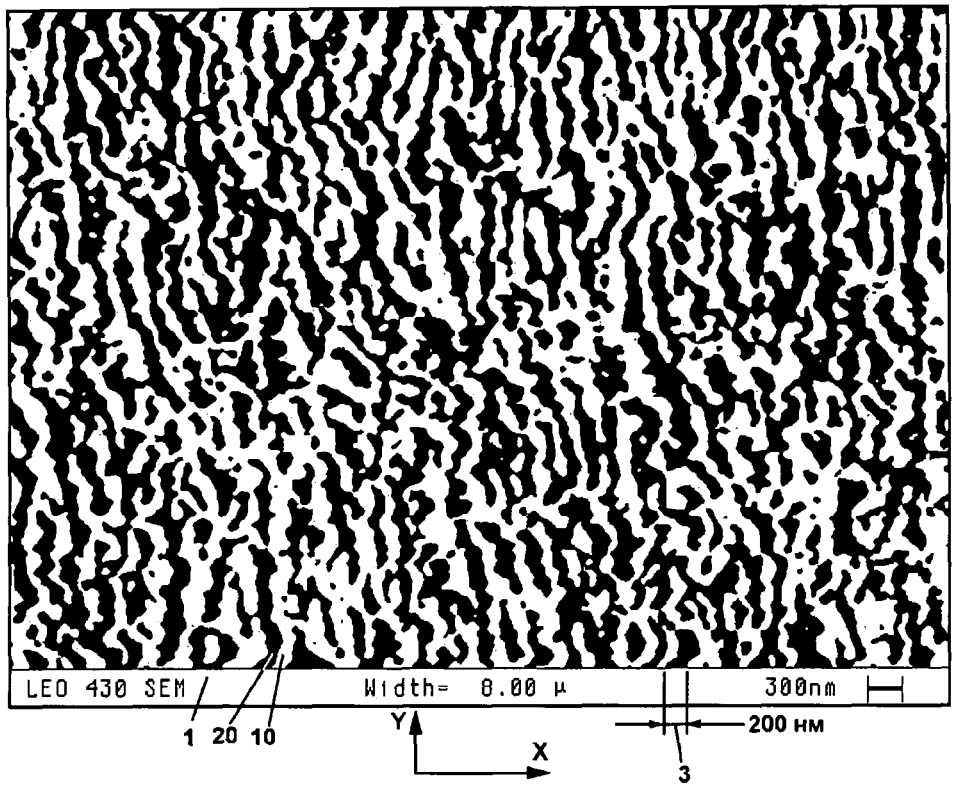
FIG. 1A is a scanning electron microscope (SEM) top view of a wave ordered structure (WOS) nanomask having an average period of 200 nm formed on a surface of an aluminum substrate using a $N_2^+$ oblique ion beam with energy E=5 keV, according to the invention.

FIG. 1A shows an SEM image with enhanced contrast (without halftones) of a top view of a self-forming wave ordered structure (WOS) formed on a surface of aluminum substrate at room temperature using a $N_2^+$ ion beam with energy E=5 keV at an angle of bombardment θ=53° from surface normal with ion fluence of $10^{18}$ $cm^{-2}$ and ion current density of 0.1 mA/$cm^2$. The WOS is a wavelike nanomask 1 with an average period 3 (wavelength π=200 nm). The horizontal field width of the SEM image is 8 μm. White stripes 10 and black stripes 20 are the opposite slopes of the waves of the WOS-nanomask. One can see the considerable line edge roughness in the WOS-nanomask pattern, which is due to the polycrystalline grain nature of aluminum.

Figure 1B:
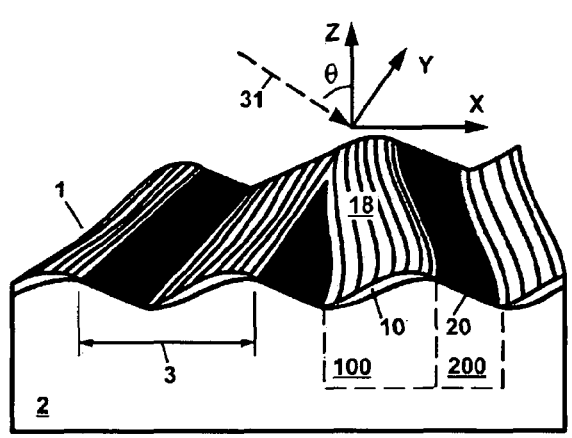
FIG. 1B is a schematic perspective view of separated and connected elongated elements of a WOS-nanomask and their cross-section, according to the invention.

FIG. 1B shows a perspective, cross-sectional view of separated and connected elements of the WOS-nanomask with a cross section of waves in the XZ plane on the surface of aluminum 2. The location of the wave slopes 10 and 20 and their orientation are the same as in FIG. 1A (which corresponds to the XY plane). Wave crests are on average parallel to the Y axis, i.e., the array of waves is anisotropic. A single wave (nanomask element) in the cross-section has an inner region of aluminum that includes a first part 100 and a second part 200. The wave also has an outer region of aluminum nitride that includes a first part 10 and a second part 20 with a lower content of implanted nitrogen atoms. Regions 10 and 20 are formed from aluminum by irradiation using a beam of nitrogen ions. In at least some embodiments, the ions of the beam have energy in the range from 0.5 to 8 keV during nanomask formation. In cross-section the regions 10 and 20 are connected to each other at a wave crest or peak. The slopes of the waves of WOS-nanomask 1 are preferably tilted symmetrically relative to the XY plane. In some embodiments, the slopes are at an angle of about 30°. In at least some embodiments, the thickness of regions 20 in cross-section in XZ plane is smallest at the middle between the borders of adjacent regions 10 and gradually increases towards the borders of regions 10. The surfaces of typical joints of waves 18 were irradiated by nitrogen ion beam at near-normal incidence angles, therefore they are almost the same thickness as regions 10, and regions 18 connect regions 10 in a continuous mesh in XY plane. The thickness of regions 18 is slightly smaller than the thickness of regions 10 located parallel to the Y-axis.

The maximum thickness of region 10 for a beam of nitrogen ions, with $N^+$ ions and $N_2^+$ ions in the relative fractions of x and (1−x), respectively, is determined, in at least some embodiments, by the formula: $T=2(1+x)E$, where T is the thickness, nm, and E is the ion beam energy, keV. For atomic nitrogen ions $N^+$, the maximum thickness of the first outer region is two times greater than that for molecular ions $N_2^+$. In at least some embodiments, the nanomask is formed by the $N_2^+$ ion beam in the ion fluence (dose) range $5\times10^{16}$–$5\times10^{17}$ $cm^{-2}$. It may be preferable for the $N_2^+$ ion beam to use the fluence (dose) range $1\times10^{17}$–$5\times10^{17}$ $cm^{-2}$.

As seen in FIG. 1A, the waves of nanomask 1 have rough edges, breaks, bends, and branches, i.e. connections with each other. Generally, the waves are elongated along the Y-axis and these elongated elements have a length in the range of, for example, 3λ to 5λ. At the same time there are elements having more or less elongation as well as subwavelength point-like elements with a size of less than λ. In general, the array of waves is quasiperiodic and substantially anisotropic. In at least some embodiments, the period is selected from the range from 20 to 200 nm or 20 to 400 nm. A distinctive feature of the wavelike nanomask is that its pattern does not contain repeating parts with the same relative positions of the elements, which is due to the self-forming nature of the nanomask.

A characteristic feature of the topology of nanomask 1 in FIG. 1A is that the regions 10 of some elements are connected to each other, and regions 20 of some elements are also connected to each other, to form a branched structure or a mesh. At the same time there are both separated regions 10 and separated regions 20.

The WOS-nanomask shown in FIGS. 1A to 1B can be formed on the aluminum surface by irradiation of the aluminum with a beam of nitrogen ions $N_2^+$. In one example, the nanomask is formed using a beam having energy of 5 keV and directed in the XZ plane of incidence along the arrow 31 at an angle θ=53° from Z-axis. The projection of ion flow 31 on the XY plane is along the X-axis in this example.

During sputtering of aluminum by nitrogen ions a self-forming process takes place resulting in the formation of wavelike nanomask 1. In one example, the nanomask formation depth or the depth of sputtering $D_F$=150 nm from the initial level of the silicon surface. In the example, the regions 10 are bombarded by nitrogen ions at near normal angles, and regions 20 are bombarded at glancing angles, which determines the thickness of the regions 10 and 20. Crests of nanomask waves in an array can be predominantly oriented perpendicular to the projection of ion flow on the surface of aluminum, (e.g., perpendicular to the X-axis when the ion flow projection is along the X-axis). In at least some embodiments, with decreasing ion energy and increasing ion bombardment angle θ measured from surface normal (Z-axis) the wavelength λ or period 3 of the array can be reduced.

Ion energy can range from, for example, 0.5 to 4 keV for $N^+$ ions and from, for example, 1 to 8 keV for $N_2^+$ ions. Such energy ranges may result in a nanomask period in the range from 20 to 200 nm (or 20 to 400 nm). With ion energies greater than 8 keV and using $N_2^+$ ion beam, one can form the nanomasks with the periods larger than 200 or 400 nm.

Figure 1C:
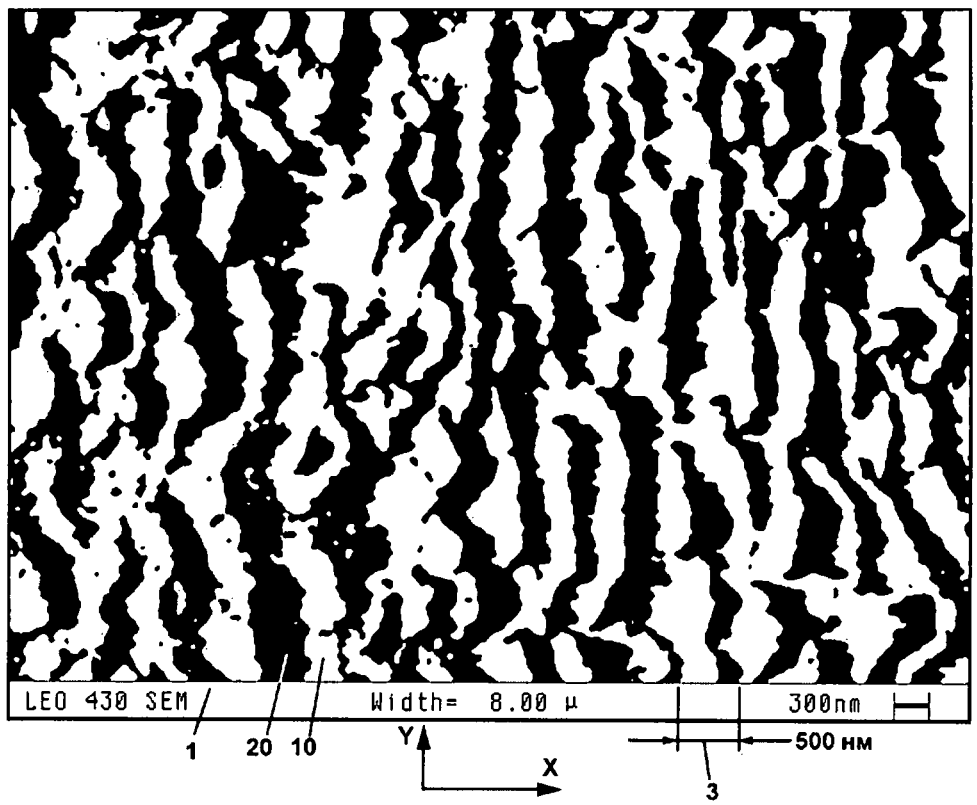
FIG. 1C is a scanning electron microscope (SEM) top view of a WOS-nanomask having an average period of 500 nm formed on a surface of an aluminum substrate using a $N_2^+$ oblique ion beam with energy E=5 keV, according to the invention.

In at least some embodiments, the period of the WOS-nanomask 1 is time (or ion fluence or ion dose) dependent. FIG. 1C shows an SEM image with enhanced contrast (without halftones) of a top view of a WOS-nanomask formed on a surface of aluminum substrate at room temperature using a $N_2^+$ ion beam with energy E=5 keV at an angle of bombardment θ=53° from surface normal with a greater ion fluence of $5\times10^{18}$ $cm^{-2}$ and ion current density of 0.1 $mA/cm^2$. One can see that a 5× increase in ion fluence resulted in 2.5× increase in WOS-nanomask period compared with FIG. 1A.

Figure 1D:
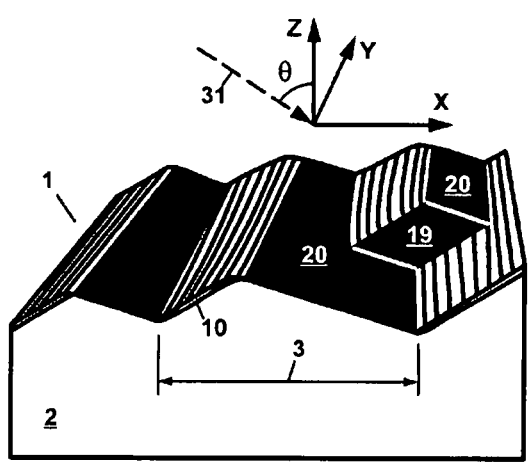
FIG. 1D is a schematic perspective view of separated elongated elements of a WOS-nanomask including the end of the element and their cross-section, according to the invention.

FIG. 1D is a perspective view of separated elongated elements of a WOS-nanomask including the end of the element and their cross-section. End surfaces of typical wave breaks 19 were irradiated by the beam of nitrogen ions at grazing angles of about 70° or more, therefore they are almost the same thickness as regions 20 and connect regions 20 in a continuous mesh.

It should be noted that regions 20 does not form in all cases, for example, they may be absent for large grazing angles of ion incidence θ>65° to the initial aluminum surface. In contrast, for WOS-nanomasks at the stage of wave slope angles' growth, both regions 10 and regions 20 occur, and during the increase in wave slope angles the thickness of regions 10 increases and the thickness of regions 20 decreases.

FIG. 2A shows schematically sequential cross-sectional views of the formation of multiple WOS-nanomask, conical elements and a layer of hollow nanospheres on, for example, an aluminum surface during ion sputtering by $N_2^+$ ion beam. Ion energy and incidence angle can be set as E=5 keV and θ=65°. The ion beam current density may be, for example, of about J=1 $mA/cm^2$. It should be noted that such a powerful ion beam may provide heating of aluminum substrate to near the melting temperature, and ion sputtering in combination with thermal effects may facilitate the formation of hollow metal nanospheres. In case of, for example, titanium having higher melting temperature a larger ion current density may be required, for example, J=3 $mA/cm^2$ and/or a substrate with a titanium layer on glass or ceramic with low thermal conductivity may be used to get higher temperature and/or additional heaters can be applied.

Initially oblique ion bombardment of aluminum substrate 2 with nitrogen ion beam results in the formation of WOS-nanomask 1 on aluminum surface. In at least some embodiments, the surface temperature of the structure 400 may not exceed 100-150° C. due to low ion fluence and WOS-nanomask formation is not considerably affected by thermal mass transfer. Thus, the WOS-nanomask in the structure 400 can be similar to that shown in FIGS. 1A to 1D and formed at room temperature by $N_2^+$ ion beam having a relatively weak current density of J=0.1 $mA/cm^2$. In this particular example, the nanomask period is reduced to about 100 nm due to the larger incident angle of θ=65°.

A further increase in ion fluence leads to the fragmentation of the wave like nanomask and to the formation of conical structures as shown in structure 401. Ion sputtering in combination with thermal mass transfer and the grain nature of the metal may induce nanomask fragmentation and formation of cones 30 with aluminum nitride tops 10a and sidewall surfaces 20a. The cones are substantially directed towards the ion beam. The temperature of the cone tops may be high enough, for example, about 550° C., to initiate blistering (for example, the formation of aluminum bubbles or hollow metal nanospheres 21 filled with nitrogen gas) as shown in structure 402.

The phenomena of blistering and exfoliation are known for noble gas ions (see, for example, Chapter 7 in the book Sputtering by Particle Bombardment II: Sputtering of Alloys and Compounds, Electron and Neuron Sputtering, Surface Topography, Edited by R. Behrisch, 1983, Springer-Verlag, Berlin-Heidelberg-New York-Tokyo, 391 pages, incorporated herein by reference). It is known that the thickness of the blister walls can be equal to or larger than ion projection range in the metal $R_P$. However, the known blistering phenomena typically result in substantially flat blisters and exfoliation. It is believed that the present nanostructured layer of hollow metal nanospheres which are created by chemically active ions forming chemical compounds with the metal is not previously known.

During ion sputtering the nanospheres 21a may grow in size and smaller blisters 22 may appear as shown in structure 403. Pits 12 may occur on the bottoms of the nanospheres due to aluminum diffusion and evaporation to the walls inside the nanospheres. Although not wanting to be limited to a particular theory, it is thought that during ion sputtering the nanospheres may grow due to the plastic deformation of their ultra thin aluminum shells, through which the flow of nitrogen penetrates at near melting temperature thus increasing the internal gas pressure. The ultra-thin aluminum shells include aluminum nitride synthesized from aluminum using the nitrogen ion beam. Along with the growth of nanospheres 21a, smaller nanospheres 22a may form both inside and outside the larger nanospheres 21a and a nanostructured layer of metal nanospheres forms as shown in structure 404. In addition, small pores 13 may occur both inside and outside the nanospheres 21a and pits 12a may deepen due to aluminum diffusion and evaporation to the walls inside the nanospheres. In at least some embodiments, the small pores 13 may have a fine porous structure. In at least some embodiments, the surface of the nanospheres may be rough and their shape may be irregular.

In at least some embodiments, the thickness 5 of the nanosphere walls can be determined by the ion range $R_P$, for example, in one example this thickness was about 10 nm for $N_2^+$ ions at an energy of 5 keV. However, this thickness can be larger than $R_P$ due to nitrogen diffusion in aluminum and it can be smaller than $R_P$ due to plastic deformation of the nanosphere walls. In addition, diffusion migration of aluminum and its evaporation can result in wall roughening and wall thickness variations.

In at least some embodiments, the average diameter 4 of the nanospheres can be substantially determined by their initial positions, which in turn is given by the period 3 of WOS-nanomask. However, the nanosphere diameter 4 may depend on factors such as, for example, the ultimate strength of the metal, wall thickness 5, and gas pressure inside the nanosphere. When the pressure of nitrogen in an aluminum nanosphere approaches the value on the order of, for example, $10^8$ Pa, the nanosphere may burst and the parts 23 of the broken nanosphere may appear in the nanostructured layer as in illustrated in structure 405. Secondary nanospheres 24 may form from these nanosphere shells as illustrated in structure 406. In this structure larger pits 12b and nanospheres 22b may develop.

FIG. 2B shows cross-sectional views of additional features that may appear along with the formation of hollow metal nanospheres. In at least some embodiments, hollow conical features 31 may form on tops of cones 30 during ion bombardment of the aluminum substrate 2. These hollow conical features together with cones are substantially directed towards the ion beam as shown in the structure 402a. In at least some embodiments, multichamber structures 21d made up from connected hollow nanospheres may form. As shown in structure 406a, some nanospheres or chambers of these multichamber structures may be supported by protrusions 30a, which may be the bases of cones 30. In some embodiments, the layer of hollow nanospheres follows the surface profile of the rough substrate surface, which includes protrusions 30b, as shown in structure 406b. In at least some embodiments, the hollow metal nanospheres can be elongated and substantially directed towards the ion beam. In at least some embodiments, each hollow metal nanosphere is connected to the substrate or to the adjacent hollow metal nanospheres or both.

Figure 3A:
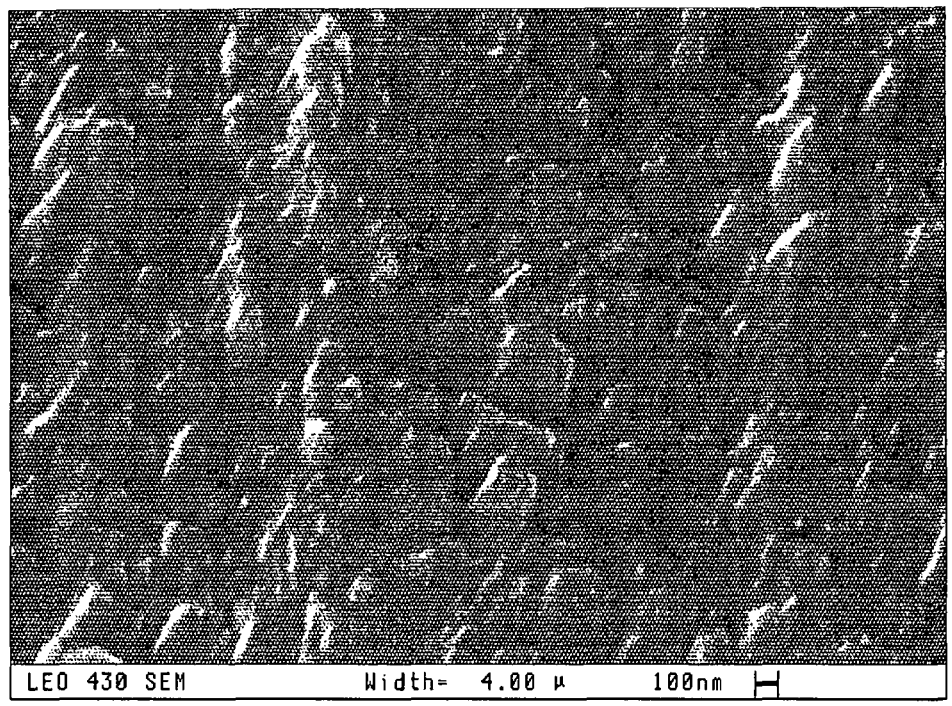
FIGS. 3A to 3D are SEM top views of conical features formed on the surface of an aluminum substrate using a $N_2^+$ low-power oblique ion beam with energy E=5 keV at substrate temperatures of 150, 350, 400, and 500° C., respectively, according to the invention.
Figure 3B:
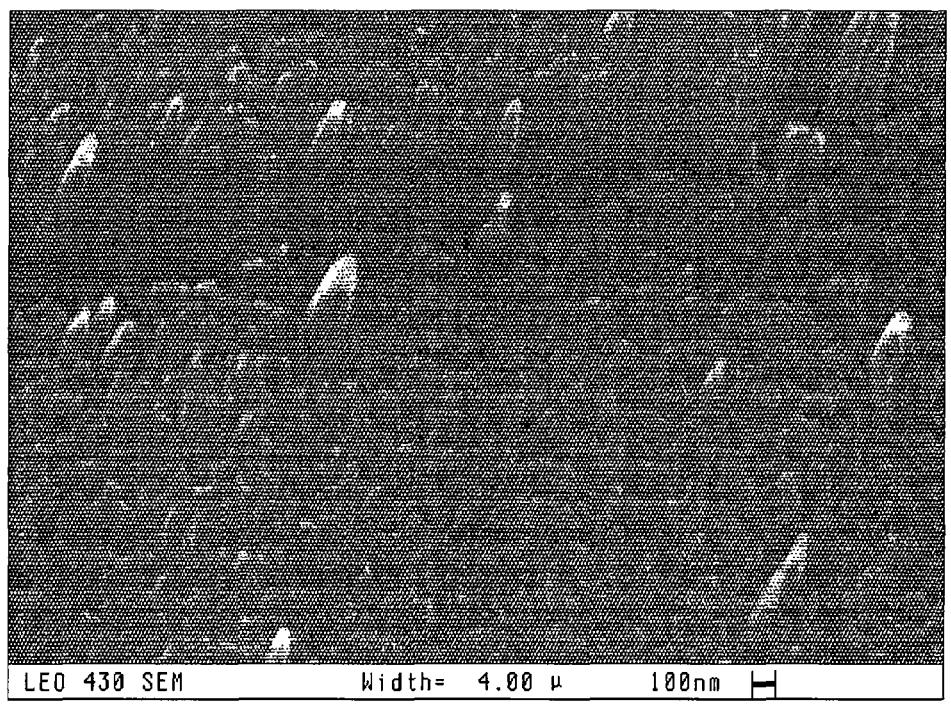
Figure 3C:
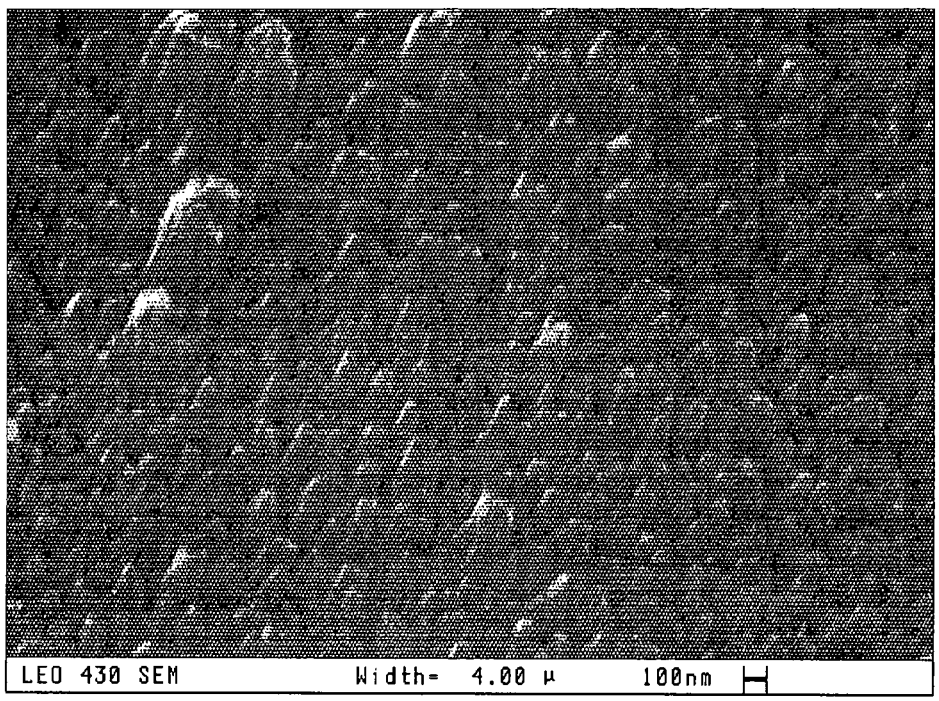
Figure 3D:
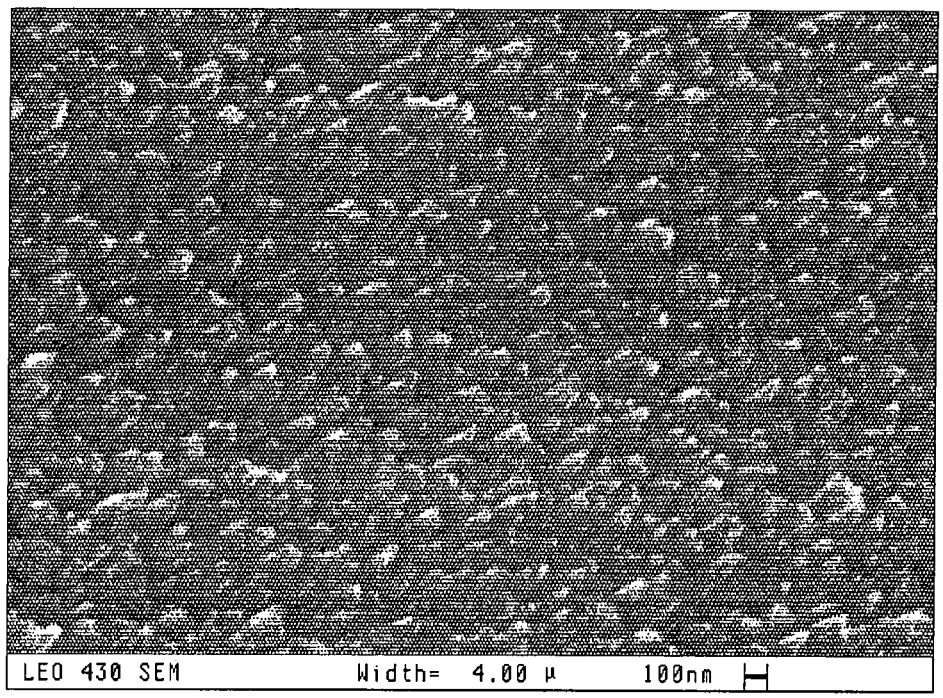

In some embodiments, the surface of aluminum substrate may be sputtered by a low-power ion beam, which does not result in substrate heating. In these embodiments the substrate may be heated by a resistive heating element or by lamps. FIGS. 3A to 3D show SEM top views of conical features formed on the surface of aluminum substrate using a $N_2^+$ low-power ion beam with energy E=5 keV at an angle of bombardment θ=53° from surface normal with ion fluence of $5 \times 10^{17}$ cm$^{-2}$ and ion current density of 0.1 mA/cm$^2$ at different substrate temperatures of 150, 350, 400, and 500° C., respectively. It can be seen that, in contrast to room temperature, at which the wave-like nanomask forms, an elevated temperature can lead to the formation of dense conical features. Note that the nanospheres may appear on the tops of some cones yet at 350° C. as is seen in FIG. 3B. In at least some embodiments, the minimum substrate temperature at which the nanospheres start to form is $\frac{2}{3}T_m$, where $T_m$ is melting point temperature of the metal measured in Kelvin. For example, for aluminum $T_m$=933 K=660° C. and 350° C.=623 K=$\frac{2}{3}T_m$.

Figure 3E:
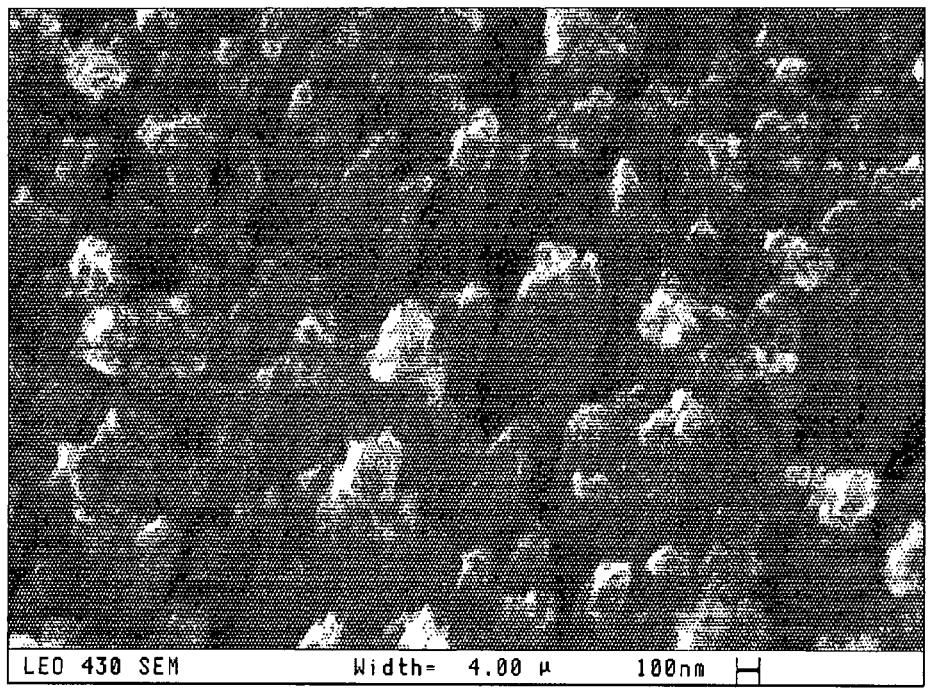
FIG. 3E is a SEM top view of conical features with hollow nanospheres formed on the surface of an aluminum substrate using a $N_2^+$ low-power oblique ion beam with E=5 keV at a substrate temperature of about 550° C., according to the invention.
Figure 3F:
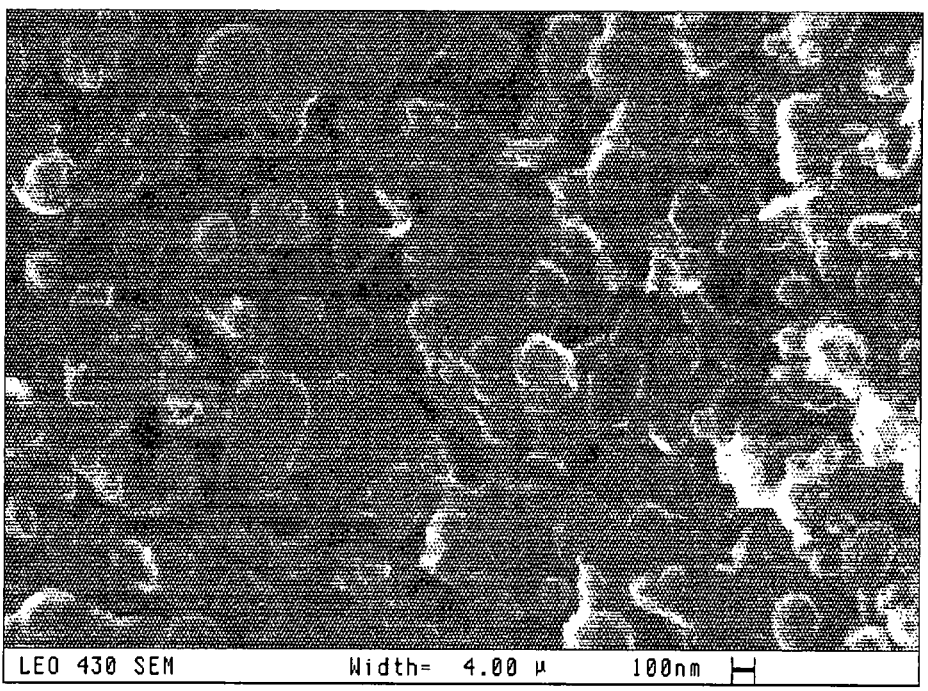
FIG. 3F is a SEM top view of a layer of hollow nanospheres formed on the surface of an aluminum substrate using a $N_2^+$ low-power oblique ion beam with E=5 keV at the substrate temperature of about 550° C., according to the invention.

At higher substrate temperature of about 550° C., hollow nanospheres begin to form densely as shown in FIGS. 3E and 3F, which correspond to the different areas of the same aluminum substrate irradiated by the $N_2^+$ ion beam with the E=5 keV and incident angle θ=53° with ion fluence of $5 \times 10^{17}$ cm$^{-2}$ and ion current density of 0.1 mA/cm$^2$. One can see that some nanospheres in FIG. 3F are elongated along the cones of FIG. 3E. The size of nanospheres in this particular example ranges from 50 to 350 nm.

Figure 4A:
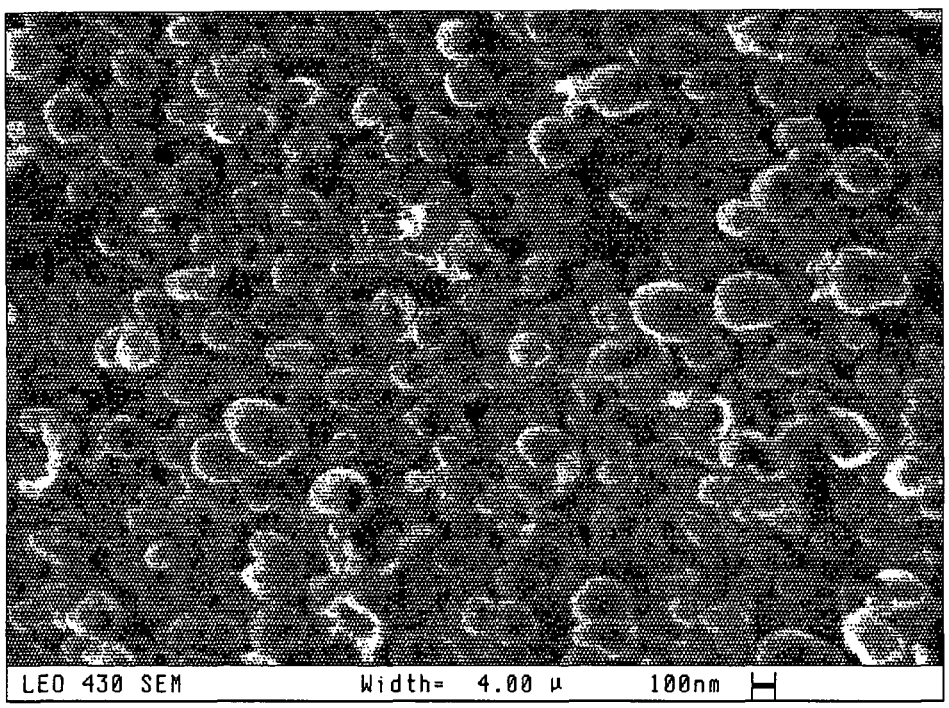
FIG. 4A is a SEM top view of a layer of hollow nanospheres formed on the surface of an aluminum substrate using a $N_2^+$ high-power oblique ion beam with energy E=5 keV and incident angle θ=53°, according to the invention.
Figure 4B:
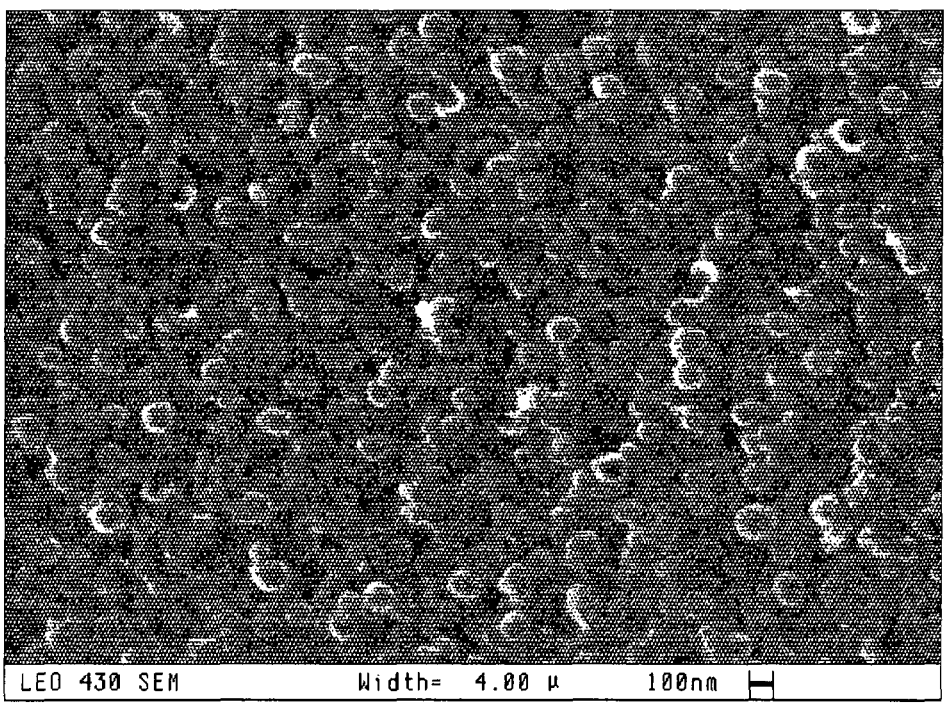
FIG. 4B is a SEM top view of a layer of hollow nanospheres formed on the surface of an aluminum substrate using a $N_2^+$ high-power oblique ion beam with energy E=3 keV and incident angle θ=53°, according to the invention.
Figure 4C:
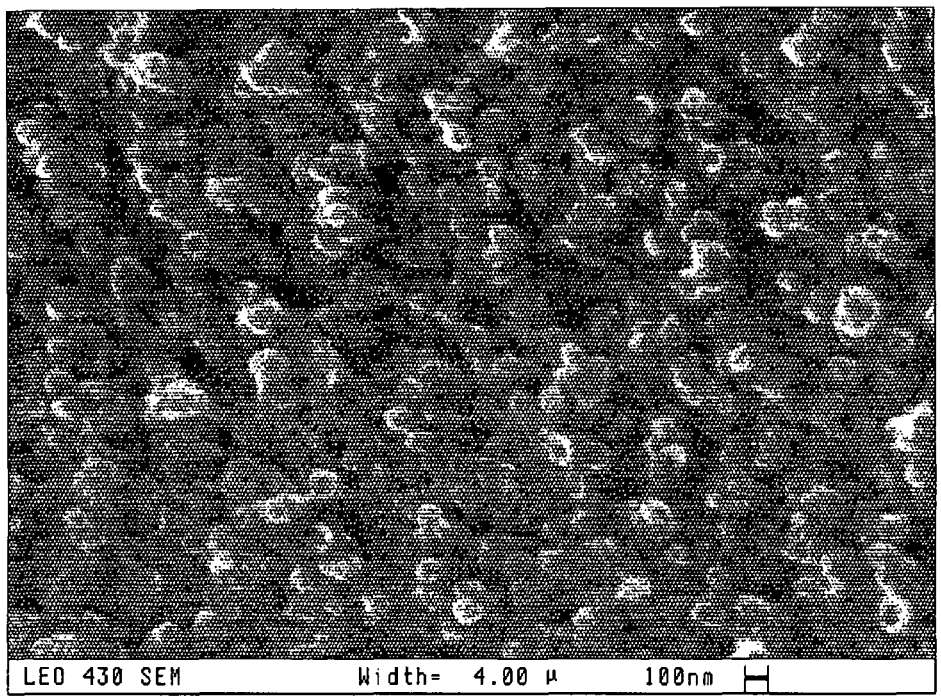
FIG. 4C is a SEM top view of a layer of hollow nanospheres formed on the surface of an aluminum substrate using a $N_2^+$ high-power oblique ion beam with energy E=5 keV and incident angle θ=65°, according to the invention.

The nanosphere size may be controlled, at least in part, by ion energy and incidence angle as illustrated in FIGS. 4A to 4C, which are SEM top views of the layer of hollow aluminum nanospheres formed on the surface of an aluminum substrate using a $N_2^+$ ion beam with ion fluence of $5 \times 10^{17}$ cm$^{-2}$ and ion current density of 1 mA/cm$^2$ for different E and θ: E=5 keV θ=53° (FIG. 4A), E=3 keV θ=53° (FIG. 4B), and E=5 keV θ=65° (FIG. 4C). The size of the nanospheres in FIG. 4A is 50 to 350 nm, and it is reduced to 50 to 150 nm in FIGS. 4B and 4C. The lower the ion energy or the higher angle of ion incidence, the smaller is the diameter of nanospheres. In addition, the lower ion energy often results in the thinner walls of nanospheres due to the shorter ion projection range, $R_P$.

Figure 5:
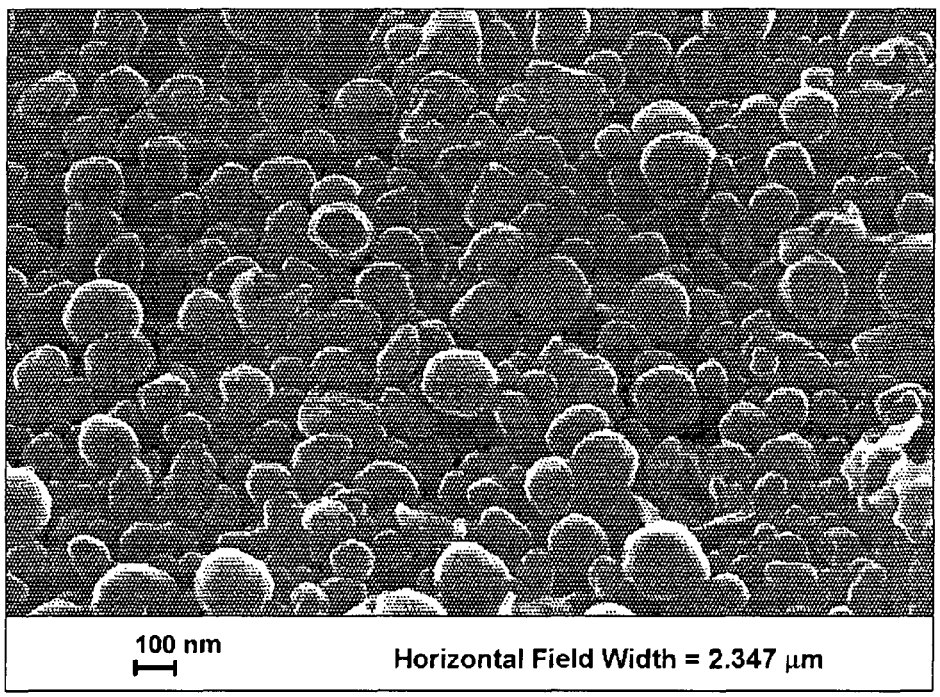
FIG. 5 is a SEM view, angled at 45°, of a layer of hollow substantially closed nanospheres formed on the surface of an aluminum substrate using a $N_2$ high-power oblique ion beam with energy E=5 keV and incident angle θ=53°, according to the invention.

FIG. 5 shows a SEM view, angled at 45°, of the layer of hollow substantially closed nanospheres formed on the surface of an aluminum substrate using a $N_2^+$ ion beam with energy E=5 keV at an angle of bombardment θ=53° from surface normal with ion fluence of $2\times10^{17}$ cm$^{-2}$ and ion current density of 1 mA/cm$^2$. The size of nanospheres is 50 to 200 nm. The lower ion fluence may result in smaller nanospheres as well.

Figure 6A:
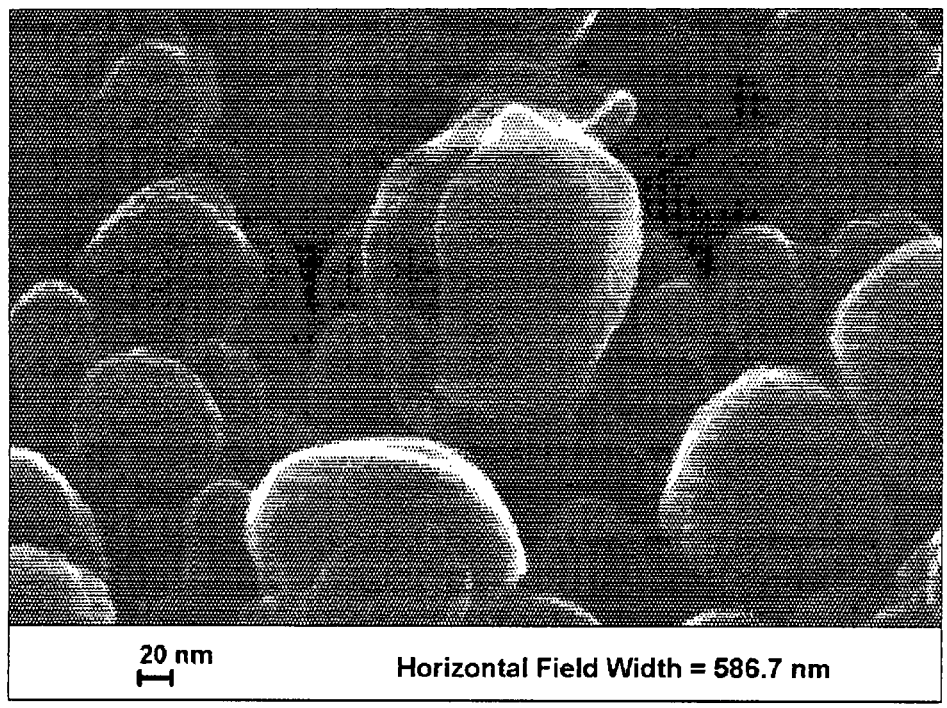
FIG. 6A is a SEM view, angled at 45°, of an opened nanosphere in a layer of hollow substantially closed nanospheres formed on the surface of an aluminum substrate using a $N_2^+$ high-power oblique ion beam with energy E=5 keV and incident angle θ=53°, according to the invention.
Figure 6B:
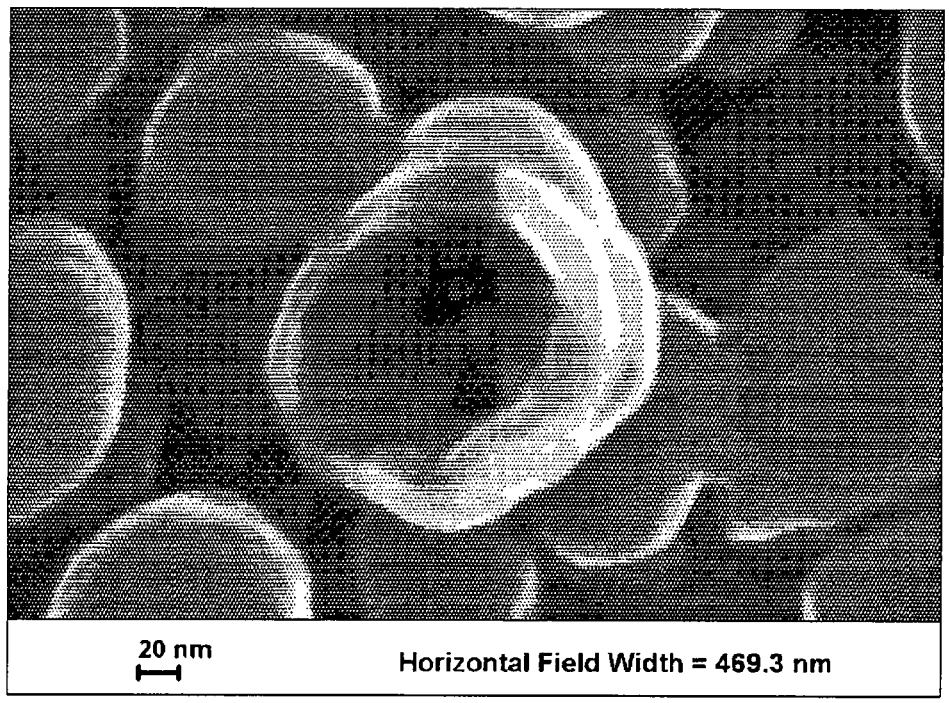
FIG. 6B is a SEM top view of an opened nanosphere in a layer of hollow substantially closed nanospheres formed on the surface of an aluminum substrate using a $N_2^+$ high-power oblique ion beam with energy E=5 keV and incident angle θ=53°, according to the invention.

FIGS. 6A to 6B show SEM views of opened nanospheres in a layer of hollow substantially closed nanospheres formed on the surface of an aluminum substrate using a $N_2^+$ ion beam with energy E=5 keV and incident angle θ=53° with ion current density of 1 mA/cm$^2$ and ion fluencies of $2\times10^{17}$ and $5\times10^{17}$ cm$^{-2}$, respectively. The thickness of the nanosphere walls is 10 to 20 nm. In FIG. 6B, the rough inner walls of the opened nanosphere and pits on its bottom are shown.

Figure 7A:
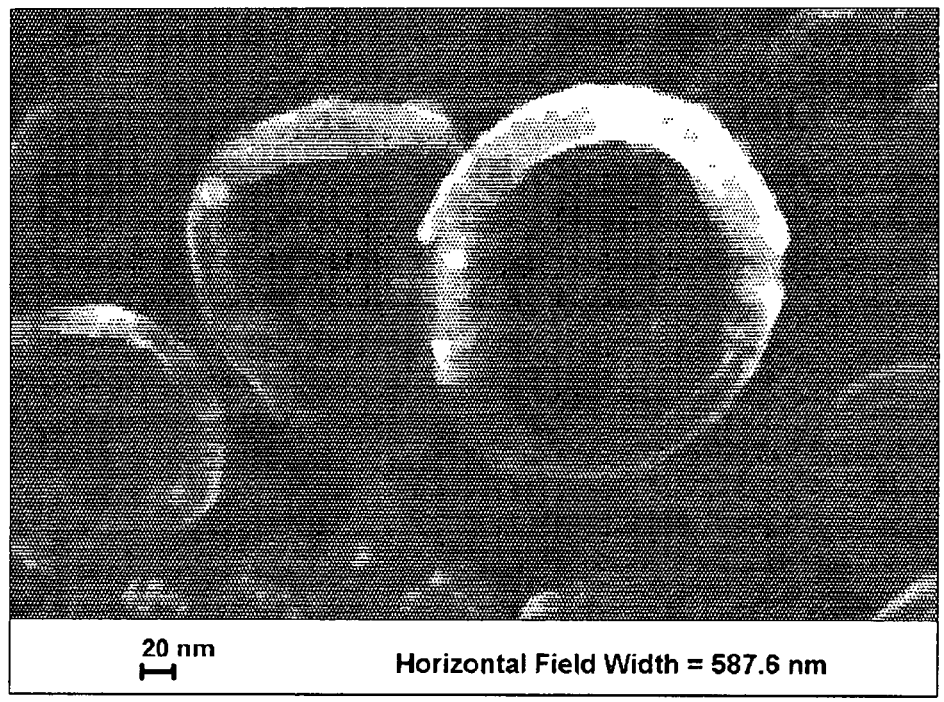
FIGS. 7A to 7B are SEM views, angled at 30°, of a layer of substantially opened hollow nanospheres initially formed on the surface of an aluminum substrate using a $N_2^+$ high-power oblique ion beam with energy E=5 keV and incident angle θ=53° and then opened by ion sputtering using a low-power oblique ion beam, according to the invention.
Figure 7B:
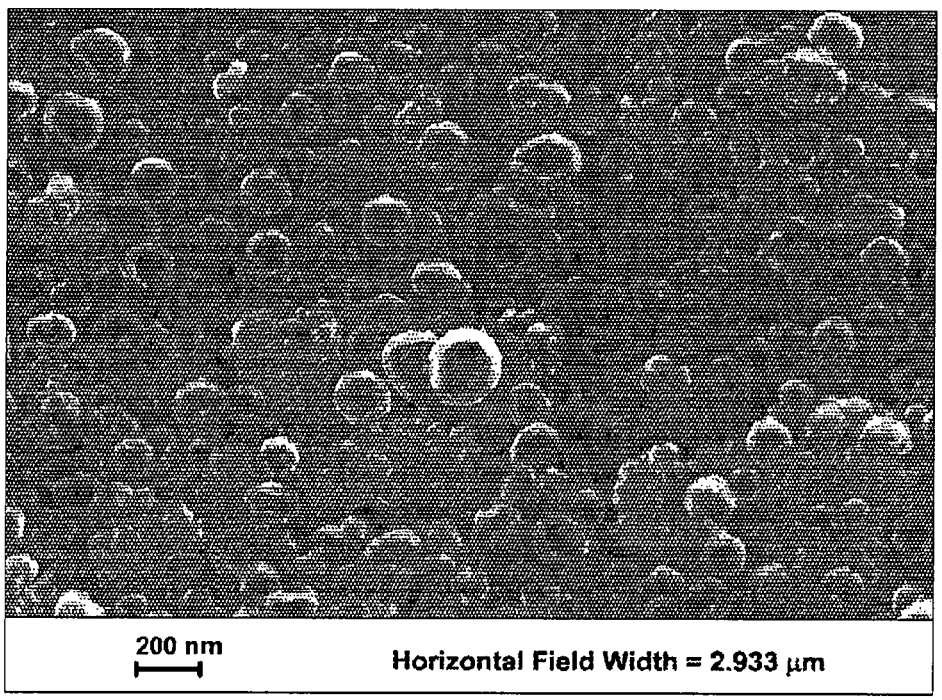

In some embodiments it is preferable to use a layer of substantially opened hollow metal nanospheres, as illustrated in FIGS. 7A to 7B. The layer of opened metal nanospheres can be formed by two-step ion sputtering process. At the first step, a layer of substantially closed hollow nanospheres is formed on the surface of, for example, an aluminum substrate using, for example, a $N_2^+$ ion beam with energy E=5 keV and incident angle θ=53° with ion fluence of $5\times10^{17}$ cm$^{-2}$ and ion current density of 1 mA/cm$^2$. At the second step, the nanospheres can be opened by ion sputtering using a low power ion beam. In one example, the nanospheres were sputtered to the equivalent depth of about 40 nm using a $N_2^+$ ion beam with energy E=5 keV and incident angle θ=34° and weak ion current density of 0.1 mA/cm$^2$ to not heat the surface and to suppress thermal mass transfer. In this example, at the second sputtering step the projection of the ion beam at the substrate surface was the same as in the first step. Instead of nitrogen, any type of ion can be used at the second step including noble gas ions, for example, argon.

FIGS. 7A to 7B illustrate that the nanospheres in the nanostructured layer are typically thin-walled and hollow. In addition, in FIG. 7A a fine porous structure with pore size 10 to 20 nm is visible between the opened nanospheres and inside the nanospheres at their bottoms. This fine porous structure, which includes pores 13 illustrated in FIGS. 2A and 2B, can often be opened by ion sputtering using a low power ion beam.

Figure 8A:
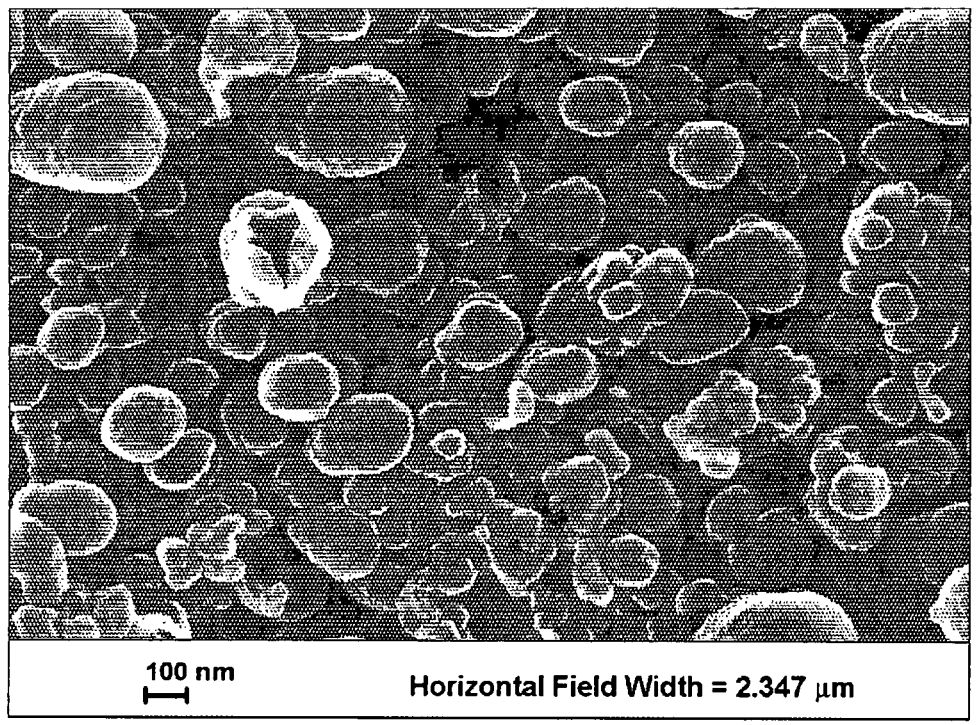
FIG. 8A is a SEM top view of a layer of hollow substantially closed nanospheres formed on the surface of a 0.7-μm-thick aluminum film on a silicon substrate using a $N_2^+$ high-power oblique ion beam with energy E=5 keV and incident angle θ=53°, according to the invention.
Figure 8B:
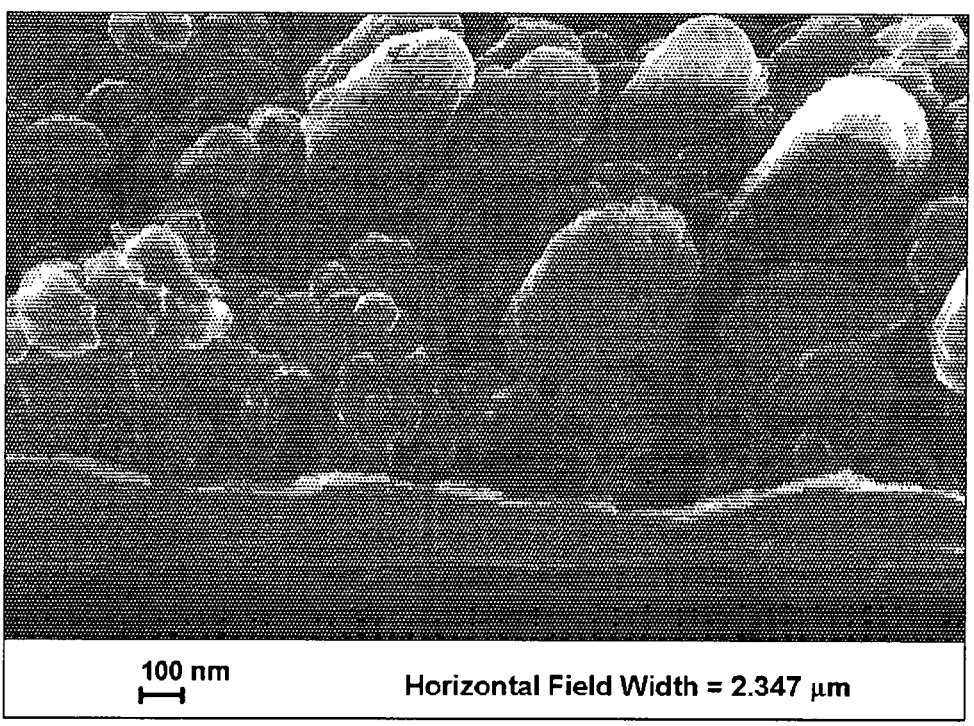
FIG. 8B is a SEM view, angled at 70°, of a cleaved silicon substrate with a layer of hollow substantially closed nanospheres formed on the surface of a 0.7-μm-thick aluminum film on a silicon substrate using a $N_2^+$ high-power oblique ion beam with energy E=5 keV and incident angle θ=53°, according to the invention.

In some embodiments a layer of metal hollow nanospheres can be disposed on the surface of a metal film on nonmetal carrier. In one example a nanostructured layer of hollow substantially closed aluminum nanospheres was formed on the surface of a 0.7 μm-thick aluminum film deposited on a silicon plate with a top layer of thermal SiO$_2$ (SiO$_2$/Si structure). The nanostructured layer was formed using a $N_2^+$ ion beam with energy E=5 keV and incident angle θ=53° with ion fluence of $5\times10^{17}$ cm$^{-2}$ and ion current density of 1 mA/cm$^2$. The top view of the nanostructured layer and angled view of a cleaved silicon plate with the layer are shown in FIGS. 8A and 8B, respectively. FIG. 8B shows nanospheres with elongation towards the ion beam.

Figure 9:
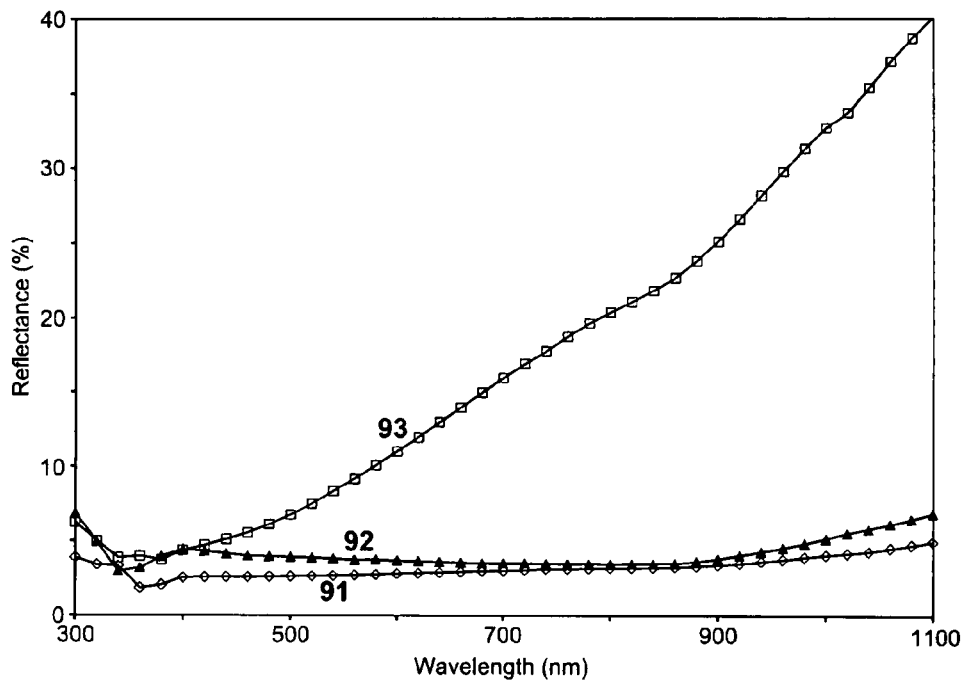
FIG. 9 are graphs of the wavelength-dependent reflectance of a layer of hollow substantially closed nanospheres formed on the surface of an aluminum substrate and a 0.7-μm-thick aluminum film using a $N_2^+$ high-power oblique ion beam with energy E=5 keV and incident angle θ=53°, according to the invention.

FIG. 9 shows examples of graphs of wavelength-dependent reflectance of a layer of hollow substantially closed nanospheres formed on the surface of an aluminum substrate and a 0.7-μm-thick aluminum film on a SiO$_2$/Si structure. In both examples the layers of hollow aluminum nanospheres were formed using a $N_2^+$ ion beam with energy E=5 keV and incident angle θ=53° with ion fluence of $5\times10^{17}$ cm$^{-2}$ and ion current density of 1 mA/cm$^2$. The reflectance was measured into a hemisphere for normal incident light. The graph 91 is for a layer of hollow aluminum nanospheres on a 0.7-μm-thick aluminum film on a SiO$_2$/Si structure. The graph 92 is for a layer of hollow aluminum nanospheres on an aluminum substrate. The layers of hollow aluminum nanospheres formed at ion fluence of $5\times10^{17}$ cm$^{-2}$ appear black (graphs 91 and 92). The graph of 93 is for a layer of hollow aluminum nanospheres formed at a lower ion fluence of $2\times10^{17}$ cm$^{-2}$ resulting in the formation of smaller and less dense nanospheres, which appear to be golden brown.

Figure 12:
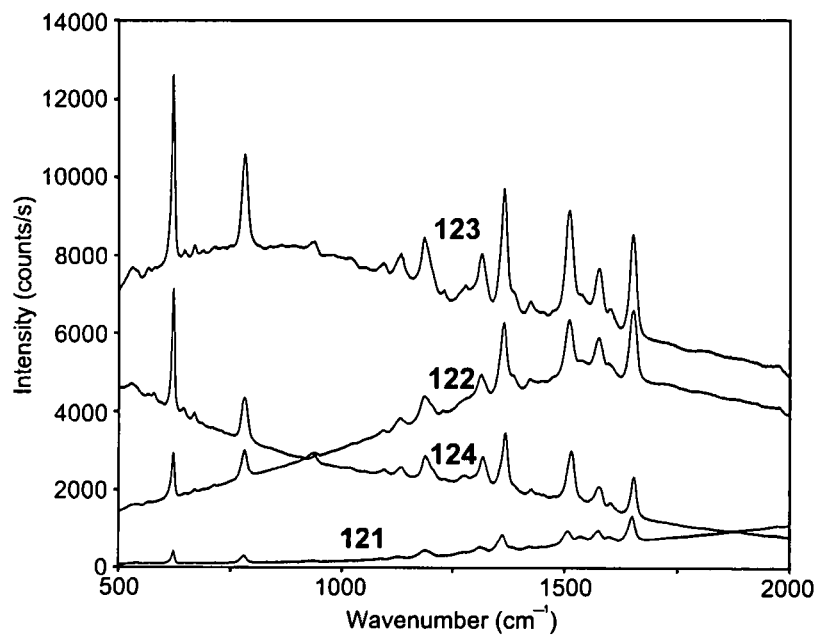
FIG. 12 are Raman spectra for rhodamine 6G (R6G) obtained from a surface of the SERS-sensor shown in FIGS. 11A and 11B, according to the invention.
Figure 13A:
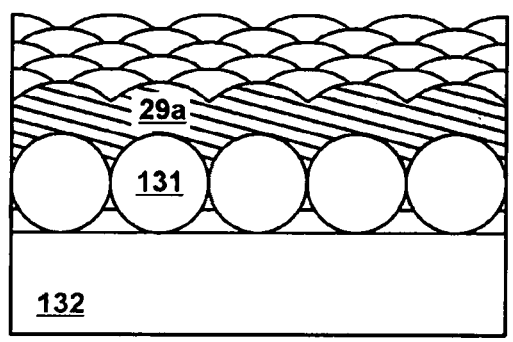
FIGS. 13A to 13B are schematic cross-sectional views of conventional SERS-sensors.
Figure 13B:
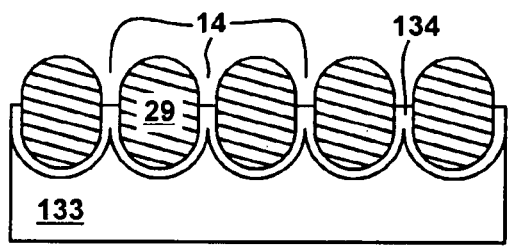

FIG. 12 shows Raman spectra for rhodamine 6G (R6G) obtained from a surface of the SERS-sensor shown in FIGS. 11A and 11B. Rhodamine molecules were deposited on a SERS-sensor surface in an amount that is equivalent to one monolayer on a flat silver surface. The laser beam diameter on the surface of the SERS-sensor was 2 μm, and the acquisition time for the spectra was 500 ms. The spectra were recorded using a Raman spectrometer for different laser power P in microwatt range and wavelength λ. Spectrum 121 is for P=19 μW and λ=488 nm. Spectrum 122 is for P=20 μW and λ=514 nm. Spectrum 123 is for P=16 μW and λ=530 nm. And spectrum 124 is for P=27 μW and Δ=568 nm. The enhancement factor of the SERS-sensors is evaluated as $10^8$ for rhodamine at P=16 μW and λ=530 nm.

Thus, the SERS-sensor having a substrate with a nanostructured layer can be fabricated in different ways in accordance with the present invention.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent is:

1. A surface enhanced Raman scattering (SERS) sensor, comprising
  a substrate having a surface and comprising a metal;
  a nanostructured layer formed on the substrate surface by an ion beam, the nanostructured layer comprising a plurality of hollow metal nanospheres, each nanosphere comprising a chemical compound formed from the metal of the substrate by the ion beam; and
  a plurality of metal elements disposed, at least in part, on the plurality of nano spheres.

2. The SERS sensor of claim 1, wherein the substrate comprises aluminum or titanium and the ion beam comprises oxygen or nitrogen ions.

3. The SERS sensor of claim 2, wherein the substrate comprises a substrate layer and an aluminum or titanium layer disposed on the substrate layer.

4. The SERS sensor of claim 1, wherein a diameter of each of the nanospheres is in a range from 20 to 400 nm.

5. The SERS sensor of claim 1, wherein the metal elements comprise at least one metal selected from a group consisting of silver, gold, copper, platinum, palladium, rhodium, ruthenium, osmium, iridium, iron, cobalt, nickel, and aluminum.

6. The SERS sensor of claim 1, wherein at least one of the metal elements is a connected metal element extending, at least in part, over a plurality of the plurality of nanospheres.

7. The SERS sensor of claim 1, wherein the substrate defines a plurality of trenches between the nanospheres and wherein at least one of the metal elements extends to at least a bottom of a one of the trenches.

8. The SERS sensor of claim 1, wherein the nanospheres have a roughened internal surface.

9. The SERS sensor of claim 1, wherein a thickness of the nanospheres is approximately equal to an ion projection range $R_p$ in the metal of the substrate.

10. A method of making a surface enhanced Raman scattering (SERS) sensor, the method comprising:
irradiating a surface of a substrate with a first ion beam to form a nanostructured layer on the substrate surface, wherein the substrate comprises a metal and the nanostructured layer comprises a plurality of hollow metal nanospheres, each nanosphere comprising a chemical compound formed from the metal of the surface by the first ion beam.

11. The method of claim 10, further comprising, prior to irradiating the surface with the first ion beam, irradiating the surface of the substrate with a second ion beam to form a plurality of conical features of the metal of the substrate.

12. The method of claim 10, wherein the metal of the substrate comprises aluminum or titanium and the first ion beam comprises oxygen or nitrogen ions.

13. The method of claim 10, wherein the substrate comprises a substrate layer and an aluminum or titanium layer disposed on the substrate layer.

14. The method of claim 10, wherein a diameter of the nanosphere is in a range from 20 to 400 nm.

15. The method of claim 10, further comprising heating the substrate to two-thirds of a melting temperature of the metal measured in Kelvin.

16. The method of claim 10, further comprising etching the nanostructured layer to open a plurality of the plurality of nanospheres.

17. The method of claim 10, further comprising depositing a plurality of metal elements over the nanostructured layer.

18. The method of claim 17, wherein depositing the plurality of metal elements comprises forming metal elements on, at least in part, tops of the plurality of nanospheres, wherein at least one of the metal elements is a connected metal element extending, at least in part, over the tops of a plurality of the plurality of nanospheres.

19. The method of claim 17, wherein the metal elements comprise at least one metal selected from a group consisting of silver, gold, copper, platinum, palladium, rhodium, ruthenium, osmium, iridium, iron, cobalt, nickel, and aluminum.

20. A nanostructured arrangement, comprising
a substrate having a surface and comprising a metal; and
a nanostructured layer formed on the substrate surface by an ion beam, the nanostructured layer comprising a plurality of hollow metal nanospheres, each of the plurality of nanospheres comprising a chemical compound formed from the metal of the substrate by the ion beam.

21. The arrangement of claim 20, wherein the plurality of nanospheres are either all substantially closed or all substantially open.

22. The arrangement of claim 20, wherein the metal of the substrate comprises aluminum or titanium and the ion beam comprises oxygen or nitrogen ions.

23. The arrangement of claim 20, wherein the substrate comprises a substrate layer and an aluminum or titanium layer disposed on the substrate layer.

24. The arrangement of claim 20, wherein a diameter of each of the plurality of nanospheres is in a range from 20 to 400 nm.

25. The arrangement of claim 20, wherein a thickness of the nanospheres is approximately equal to an ion projection range $R_P$ in the metal of the substrate.

* * * * *